(12) United States Patent
Heo et al.

(10) Patent No.: US 10,712,851 B2
(45) Date of Patent: Jul. 14, 2020

(54) ELECTRONIC DEVICE AND METHOD FOR CONTROLLING THE SAME

(71) Applicant: Samsung Electronics Co., Ltd., Suwon-si, Gyeonggi-do (KR)

(72) Inventors: Chul Joon Heo, Busan (KR); Kyung Bae Park, Hwaseong-si (KR); Yong Wan Jin, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/055,344

(22) Filed: Aug. 6, 2018

(65) Prior Publication Data

US 2019/0302937 A1    Oct. 3, 2019

(30) Foreign Application Priority Data

Mar. 30, 2018 (KR) ........................ 10-2018-0037657

(51) Int. Cl.
*G06F 3/044* (2006.01)
*G06F 3/041* (2006.01)
(Continued)

(52) U.S. Cl.
CPC ........ *G06F 3/0412* (2013.01); *A61B 5/02433* (2013.01); *A61B 5/14551* (2013.01);
(Continued)

(58) Field of Classification Search
None
See application file for complete search history.

(56) References Cited

U.S. PATENT DOCUMENTS

| 9,089,270 B2 | 7/2015 | Song et al. |
| 9,679,182 B2 | 6/2017 | Bae et al. |

(Continued)

FOREIGN PATENT DOCUMENTS

| CN | 10-7145856 A | 9/2017 |
| JP | 5713104 B2 | 5/2015 |

(Continued)

OTHER PUBLICATIONS

Extended Search Report for corresponding European Application No. 18187123.7 dated Feb. 26, 2019.

*Primary Examiner* — Carl Adams
(74) *Attorney, Agent, or Firm* — Harness, Dickey and Pierce, P.L.C.

(57) ABSTRACT

An electronic device may include an edge touch screen including a main display region and an edge display region extending from the main display region each including one or more of red pixels, near infrared ray pixels, and sensor pixels for detecting light with different wavelengths; and a controller configured to, drive the edge touch screen in response to a touch input for the edge display region being maintained for a set time by instructing at least one selected red pixel of the red pixels and at least one selected near infrared ray pixel of the near infrared ray pixels corresponding to a position of the touch input to emit light, and measure biometrics based on light amounts of light of different wavelengths received from at least one selected sensor pixel of the sensor pixels corresponding to the position of the touch input.

18 Claims, 11 Drawing Sheets

(51) Int. Cl.
  *G06F 1/16* (2006.01)
  *G06F 3/0488* (2013.01)
  *G06F 21/32* (2013.01)
  *H01L 27/32* (2006.01)
  *H04M 1/02* (2006.01)
  *A61B 5/00* (2006.01)
  *A61B 5/024* (2006.01)
  *A61B 5/1455* (2006.01)

(52) U.S. Cl.
  CPC ............ *A61B 5/6898* (2013.01); *A61B 5/742* (2013.01); *G06F 1/1626* (2013.01); *G06F 1/1643* (2013.01); *G06F 1/1652* (2013.01); *G06F 3/0488* (2013.01); *G06F 21/32* (2013.01); *H01L 27/323* (2013.01); *H01L 27/3213* (2013.01); *H04M 1/0266* (2013.01)

(56) References Cited

U.S. PATENT DOCUMENTS

| | | | |
|---|---|---|---|
| 9,699,544 B2 | 7/2017 | Song et al. | |
| 9,742,902 B2 | 8/2017 | Shimuta | |
| 9,823,771 B2 | 11/2017 | Bae et al. | |
| 9,864,448 B2 | 1/2018 | Bae et al. | |
| 9,891,746 B2 | 2/2018 | Bae et al. | |
| 9,996,179 B2 | 6/2018 | Bae et al. | |
| 2002/0079512 A1* | 6/2002 | Yamazaki | G06F 3/03545 257/200 |
| 2010/0020209 A1* | 1/2010 | Kim | H04N 5/37457 348/294 |
| 2014/0114201 A1 | 4/2014 | Watanabe et al. | |
| 2014/0213908 A1 | 7/2014 | Weng | |
| 2015/0293661 A1 | 10/2015 | Gomez | |
| 2016/0058309 A1 | 3/2016 | Han | |
| 2016/0058312 A1 | 3/2016 | Han et al. | |
| 2016/0062516 A1 | 3/2016 | Jeong et al. | |
| 2016/0213331 A1 | 7/2016 | Gil et al. | |
| 2016/0357323 A1 | 12/2016 | Kim et al. | |
| 2017/0079591 A1 | 3/2017 | Gruhlke et al. | |
| 2017/0102872 A1 | 4/2017 | Kim et al. | |
| 2017/0105633 A1 | 4/2017 | Shin | |
| 2017/0124370 A1* | 5/2017 | He | G06K 9/0012 |
| 2017/0139585 A1 | 5/2017 | Lee | |
| 2017/0164884 A1 | 6/2017 | Culbert et al. | |
| 2017/0270342 A1* | 9/2017 | He | G06F 3/042 |
| 2017/0293378 A1* | 10/2017 | Ahn | G06K 9/0002 |
| 2018/0005005 A1* | 1/2018 | He | G06F 21/83 |
| 2018/0129798 A1* | 5/2018 | He | G06K 9/0002 |
| 2019/0012512 A1* | 1/2019 | He | G06K 9/00087 |

FOREIGN PATENT DOCUMENTS

| | | |
|---|---|---|
| JP | 6107045 B2 | 4/2017 |
| KR | 10-0880392 B1 | 1/2009 |
| KR | 10-1258203 B1 | 4/2013 |
| KR | 2013-0055729 A | 5/2013 |
| KR | 10-1560282 B1 | 10/2015 |
| KR | 10-1564066 B1 | 10/2015 |
| KR | 2016-0027679 A | 3/2016 |
| KR | 2016-0144197 A | 12/2016 |
| KR | 2017-0043065 A | 4/2017 |
| KR | 10-1758047 B1 | 7/2017 |
| KR | 2017-0104419 A | 9/2017 |
| WO | WO-2015/061166 A1 | 4/2015 |

* cited by examiner

ELECTRONIC DEVICE AND METHOD FOR CONTROLLING THE SAME

CROSS-REFERENCE TO RELATED APPLICATION

This application claims priority to and the benefit of Korean Patent Application No. 10-2018-0037657 filed in the Korean Intellectual Property Office on Mar. 30, 2018, the entire contents of which are incorporated herein by reference.

BACKGROUND (a) Field

Example embodiments of the present disclosure relate to an electronic device and/or a method for controlling the same.

(b) Description of the Related Art

Recently, various types of electronic devices using a flexible display panel are developed. Electronic devices may include a display panel having respective lateral sides that are curved as well as one lateral side that is curved are released. The curved display panel may display information in a curved region, and may reduce (or, alternatively, minimize) a bezel region.

Together with an increase of interest on the healthcare field, functions for sensing biometrics and monitoring the same are added to electronic devices such as smartphones or wearable devices such as smart bands or smart watches.

Particularly, regarding the biometrics, heartbeat and/or a saturation of peripheral oxygen (SpO2) in the blood may be measured through a non-invasive optical measuring method, and a measurement module for measuring the same may be down-sized and may be mounted on various products.

The measurement module for measuring the heartbeat and the saturation of peripheral oxygen (SpO2) in the blood may be a discrete module in the electronic device, so a space for disposing other components in the electronic device may be limited.

The above information disclosed in this Background section is only for enhancement of understanding of the background and therefore it may contain information that does not form the prior art that is already known in this country to a person of ordinary skill in the art.

SUMMARY

Example embodiments are directed to conveniently measuring biometrics by use of an electronic device.

Example embodiments are directed to measuring biometrics without an additional module for measuring biometrics.

Example embodiments are directed to providing a new user experience to a user through an electronic device.

An example embodiment is related to an electronic device including: an edge touch screen including a main display region and an edge display region extending from the main display region, each of the main display region and the edge display region including one or more of red pixels, near infrared ray pixels, and sensor pixels for detecting light with different wavelengths; and a controller configured to, drive the edge touch screen in response to a touch input for the edge display region being maintained for a set time by instructing at least one selected red pixel of the red pixels and at least one selected near infrared ray pixel of the near infrared ray pixels corresponding to a position of the touch input to emit light, and measure biometrics based on light amounts of light of different wavelengths received from at least one selected sensor pixel of the sensor pixels corresponding to the position of the touch input.

In one or more example embodiments, the edge touch screen includes: a display panel including the red pixels and the near infrared ray pixels; a touch panel on the display panel, the touch panel including at least one touch sensor; a sensor panel including the sensor pixels; and a light blocking member configured to block part of the display panel from being visible to an outside of the electronic device.

In one or more example embodiments, the at least one selected near infrared ray pixel is in a region of the edge touch screen corresponding to the light blocking member.

In one or more example embodiments, the at least one selected near infrared ray pixel is in the edge display region.

In one or more example embodiments, the at least one selected near infrared ray pixel is in a portion of the main display region adjacent to the edge display region.

In one or more example embodiments, the sensor pixels are in a region of the edge touch screen corresponding to the light blocking member.

In one or more example embodiments, the sensor pixels are in the edge display region.

In one or more example embodiments, at least one of the sensor pixels extends to both the edge display region and a portion of the main display region adjacent to the edge display region.

In one or more example embodiments, the sensor pixels include: a first sensor pixel configured to detect light of a near infrared ray wavelength, and a second sensor pixel configured to detect light of a red wavelength, wherein a size of the first sensor pixel is different from a size of the second sensor pixel.

In one or more example embodiments, the red pixels and the near infrared ray pixels include organic light emitting diodes (OLEDs), and the sensor pixels includes organic photodiodes.

In one or more example embodiments, the display panel and the sensor panel are provided on a same layer.

In one or more example embodiments, the edge display region includes a left edge display region and a right edge display region extending from respective sides of the main display region, and the controller is configured to drive the edge touch screen to measure the biometrics in the left edge display region and the right edge display region in response to maintaining a multi-touch input in both the left edge display region and the right edge display region for the set time.

In one or more example embodiments, the controller is configured to drive the edge touch screen to re-measure the biometrics in response to the biometrics measured from the left edge display region and the right edge display region being different from each other.

Another example embodiment is related to a method for controlling an electronic device, the electronic device including an edge touch screen and a controller, the edge touch screen including a main display region, an edge display region extending from the main display region, each of the main display region and the edge display region including one or more of red pixels, near infrared ray pixels, and sensor pixels for detecting light with different wavelengths.

In one or more example embodiments, the method includes determining whether a touch input on the edge display region is maintained for a set time; instructing one or more selected red pixels of the red pixels and one or more selected near infrared ray pixels of the near infrared ray pixels corresponding to a position of the touch input to emit light in response to determining that the touch input is maintained for the set time; operating one or more selected sensor pixels of the sensor pixels corresponding to the position of the touch input to receive information from the selected sensor pixels, the information indicating an amount of light of the different wavelengths; and measuring biometrics based on the information.

In one or more example embodiments, the edge display region includes a left edge display region and a right edge display region extending from respective sides of the main display region, the determining includes determining, by the controller, whether a multi-touch input respectively on the left edge display region and the right edge display region is maintained for the set time, and the operating includes operating the one or more selected sensor pixels corresponding to positions of the multi-touch input in the left edge display region and the right edge display region, respectively.

In one or more example embodiments, the edge touch screen includes: a display panel including the red pixels and the near infrared ray pixels; a touch panel on the display panel, the touch panel including at least one touch sensor; a sensor panel including the sensor pixels; and a light blocking member configured to block part of the display panel from being visible to an outside of the electronic device.

In one or more example embodiments, the one or more selected infrared ray pixels is in at least one of a region corresponding to the light blocking member, the edge display region, and a portion of the main display region adjacent to the edge display region, and the sensor pixels are in at least one of the region corresponding to the light blocking member, the edge display region, and the portion of the main display region adjacent to the edge display region.

In one or more example embodiments, at least one of the sensor pixels extends to both the edge display region and the portion of the main display region adjacent to the edge display region.

In one or more example embodiments, the sensor pixels include: a first sensor pixel configured to detect light of a near infrared ray wavelength; and a second sensor pixel configured to detect light of a red wavelength, wherein a size of the first sensor pixel is different from a size of the second sensor pixel.

In one or more example embodiments, the red pixels and the near infrared ray pixels include organic light emitting diodes (OLEDs), and the sensor pixels include organic photodiodes.

According to at least one of the example embodiments, the biometrics of the user may be conveniently measured.

According to at least one of the example embodiments, the inner space of the electronic device may be efficiently used.

According to at least one of the example embodiments, the electronic device may become slim or down-sized.

According to at least one of the example embodiments, the new user experience may be provided to the user.

DETAILED DESCRIPTION

Figure 1:
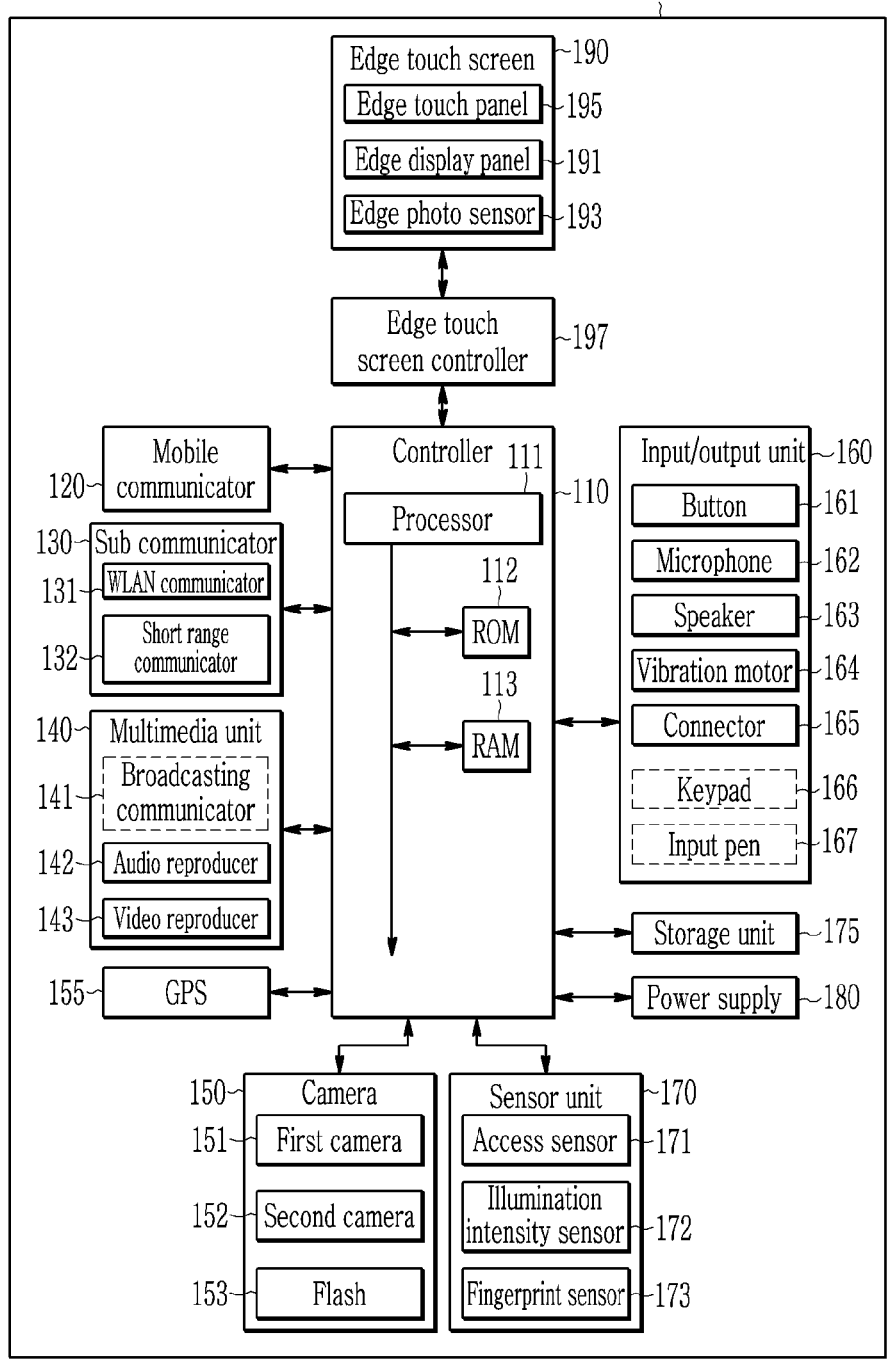
FIG. 1 shows a block diagram for an electronic device according to an example embodiment.

Example embodiments will be described more fully hereinafter with reference to the accompanying drawings, in which some example embodiments are shown. As those skilled in the art would realize, the described example embodiments may be modified in various different ways, all without departing from the spirit or scope of the example embodiments.

The drawings and description are to be regarded as illustrative in nature and not restrictive, and like reference numerals designate like elements throughout the specification.

Unless explicitly described to the contrary, the word "comprise" and variations such as "comprises" or "comprising" will be understood to imply the inclusion of stated elements but not the exclusion of any other elements. The term "unit" used in the specification signifies processing circuitry configured to execute software or hardware constituent elements such as an FPGA or an ASIC, and the "unit" performs desired (or, alternatively, predetermined) functions. However, the "unit" is not limited to the software or hardware. The "unit" may be configured to be provided in a storage medium to be addressed, or it may be configured to reproduce one or more processors. Therefore, for example, the "unit" includes constituent elements such processing circuitry executing software constituent elements, object-oriented software constituent elements, class constituent elements, or task constituent elements, and processes, functions, attributes, procedures, sub-routines, segments of program codes, drivers, firmware, micro codes, circuits, data, databases, data structures, tables, arrays, and variables. Functions provided by the constituent elements and the "units" may be combined into a lesser number of constituent elements and "units" or may be divided into additional constituent elements and "units".

The phrase "on a plane" means viewing the object portion from the top, and the phrase "on a cross-section" means viewing a cross-section of which the object portion is vertically cut from the side.

In the present specification, an "electronic device 100" signifies an electronic device including a curved display of which at least one side is bent.

Figure 2:
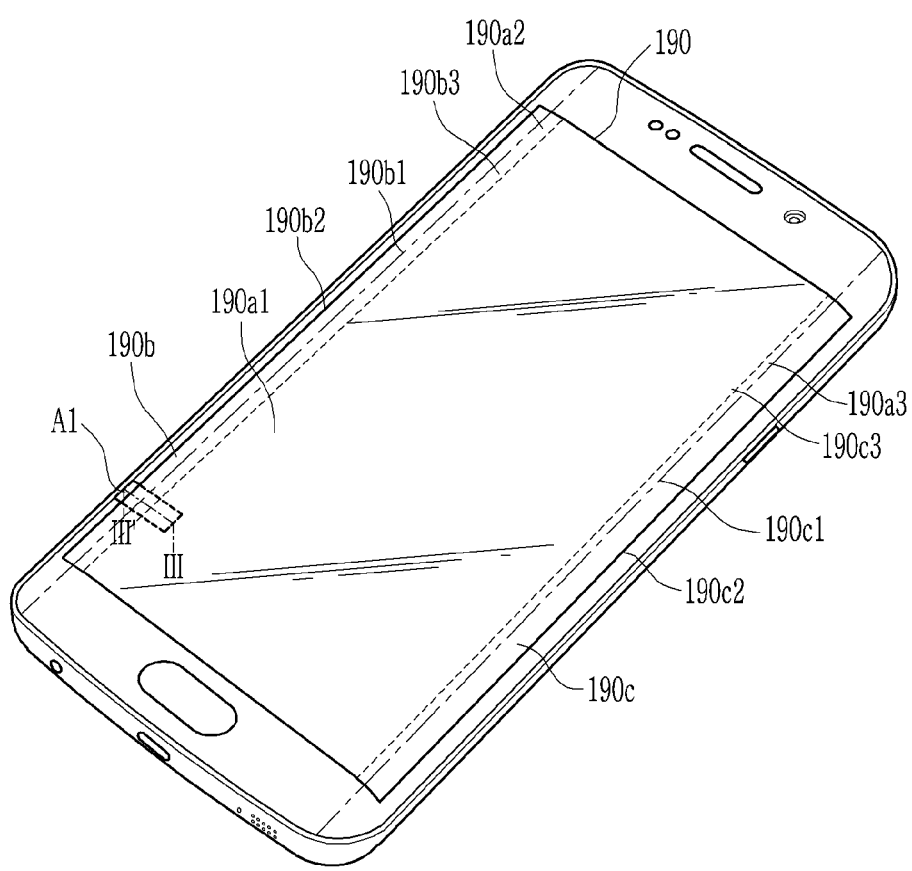
FIG. 2 shows a schematic view of an electronic device in one direction according to an example embodiment.

FIG. 1 shows a block diagram for an electronic device according to an example embodiment and FIG. 2 shows a schematic view of an electronic device in one direction according to an example embodiment.

Referring to FIG. 1 and FIG. 2, FIG. 1 is a schematic view of an electronic device according to an example embodiment in different directions, and FIG. 2 is a block diagram for an electronic device according to an example embodiment.

Referring to FIG. 1, the electronic device 100 may include a controller 110, a mobile communicator 120, a sub-communicator 130, a multimedia unit 140, a camera 150, a global positioning system (GPS) 155, an input/output unit 160, a sensor unit 170, a storage unit 175, and a power supply 180. However, example embodiments are not limited thereto, and the electronic device 100 may omit one or more of the aforementioned elements or include additional elements. Further, according to example embodiments, the electronic device 100 includes an edge touch screen 190 and an edge touch screen controller 197.

The controller 110 may include a processor 111. The controller 110 may further include a ROM 112 for storing a control program for controlling the electronic device 100, and a RAM 113 for storing signals or data input by an outside of the electronic device 100 or being used as a storage region for various tasks performed by the electronic device 100.

In an example embodiment, the term "controller" may include the processor 111, the ROM 112, and the RAM 113. Further, in some example embodiments, the term "controller" may include the edge touch screen controller 197.

The controller 110 controls an operation of the electronic device 100 and signal flows among the internal constituent elements 120 to 195 of the electronic device 100, and processes data. The controller 110 controls supplying of power to the internal constituent elements 120 to 195 by using the power supply 180. Further, when receiving an input of a user or when satisfying a desired (or, alternatively, a predetermined) condition, the controller 110 may operate a sensor of the sensor unit 170, or may perform an operating system (OS) or an application stored in the storage unit 175.

The processor 111 may include a graphic processing unit (GPU) (not shown) for processing graphic signals. The processor 111 may be realized in a System On Chip (SoC) including a core (not shown) and a GPU (not shown). The processor 111 may include a single core, a dual core, a triple core, a quad core, and a multiple thereof core. In addition, the processor 111, the ROM 112, and the RAM 113 may be connected to each other through a bus.

The processor 111 may be configured, through a layout design or execution of computer readable instructions stored in the ROM 112 and/or RAM 113, as a special purpose computer to control the mobile communicator 120, the sub-communicator 130, the multimedia unit 140, the camera 150, the GPS 155, the input/output unit 160, the sensor unit 170, the storage unit 175, the power supply 180, the touch screen 190, and/or the touch screen controller 197.

The mobile communicator 120 may be connected to another device (e.g., another electronic device, a wearable device, or a server) through a mobile communication network by using one or more antennae by control of the controller 110. The mobile communicator 120 may receive data (or content) from another device by control of the controller 110. The received data (or content) may be stored in the storage unit 175 by control of the controller 110.

The mobile communicator 120 may transmit and receive radio signals for a voice call, a video call, a short message service (SMS), a multimedia message service (MMS), and a data communication to and from a mobile phone (not shown) with an available telephone number, a smartphone (not shown), a tablet PC, or another electronic device (not shown).

The sub-communicator 130 may be connected to another device (e.g., another electronic device, a wearable device, or a server) through a wireless LAN communicator 131 and/or a short range communicator 132 by control of the controller 110. The sub-communicator 130 may receive data (or content) from another device by control of the controller 110. The received data (or content) may be stored in the storage unit 175 by control of the controller 110.

The wireless LAN communicator 131 may be wirelessly connected to an access point (AP) in a place where the AP is installed by control of the controller 110. The wireless LAN communicator 131 may include a Wi-Fi system. The wireless LAN communicator 131 supports the wireless LAN standard (IEEE802.11x) of the IEEE. The short range communicator 132 may perform a short range communication between the electronic device 100 and an external device wirelessly without an AP by control of the controller 110.

The short range communication may include a Bluetooth, a Bluetooth low energy, an infrared data association (IrDA), an ultra wideband (UWB), and a near field communication (NFC).

The electronic device 100 may include one of the mobile communicator 120, the wireless LAN communicator 131, and the short range communicator 132, or a combination of the mobile communicator 120, the wireless LAN communicator 131, and the short range communicator 132 depending on functions and/or performance. The electronic device 100 may be connected to various external accessories (e.g., a wireless speaker or a wireless headset) by using one of the mobile communicator 120 and the sub-communicator 130.

In an example embodiment, the term "communicator" includes the mobile communicator 120 and/or the sub-communicator 130.

The multimedia unit 140 may receive an external broadcasting and may reproduce audio and/or video by control of the controller 110. The multimedia unit 140 may include a broadcasting communicator 141, an audio reproducer 142, and/or a video reproducer 143.

The broadcasting communicator 141 may receive broadcasting signals (e.g., TV broadcasting signals, radio broadcasting signals, or data broadcasting signals) and additional broadcasting information (e.g., an electronic program guide (EPG) or an electronic service guide (ESG)) output by an external broadcasting station through an antenna (not shown) by control of the controller 110. Further, the controller 110 may control the received broadcasting signal and the additional broadcasting information to be reproduced by using a touch screen, a video codec (not shown), and an audio codec (not shown).

The audio reproducer 142 may reproduce an audio source (e.g., an audio file with an extension of mp3, wma, ogg or way) stored in the storage unit 175 of the electronic device 100 or received from the outside by using an audio codec by control of the controller 110.

The video reproducer 143 may reproduce a digital video source (e.g., a video file with the extension of mpeg, mpg, mp4, avi, mov, or mkv) stored in the storage unit 175 of the electronic device 100 or received from the outside by using a video codec by control of the controller 110. A multimedia application that may be installed in the electronic device 100 may reproduce the audio source or the video source by using the audio codec and/or the video codec. Further, the multimedia application that may be installed in the electronic device 100 may reproduce the video source by using a hardware codec and/or a software codec.

It will be easily understood by a person skilled in the art that various types of video codecs and audio codecs for reproducing audio/video files with various file extensions are produced and sold.

The multimedia unit 140 may exclude the broadcasting communicator 141 and may include the audio reproducer 142 and the video reproducer 143 corresponding to the performance or structure of the electronic device 100. Further, the controller 110 may be realized to include the audio reproducer 142 or the video reproducer 143 of the multimedia unit 140.

In an example embodiment, the term "audio codec" may include one or more audio codecs and the term "video codec" may include one or more video codecs.

The camera 150 may photograph a still image or video by control of the controller 110. The camera 150 may include at least one of a first camera 151 on a front side of the electronic device 100 and a second camera 152 on a rear side thereof. For example, the camera 150 may include either or both of the first camera 151 and the second camera 152. In addition, the first camera 151 or the second camera 152 may include a subsidiary light source (e.g., a flash 153) for supplying an amount of light needed to photographing.

The camera 150 may be realized to further include a first camera 151 on the front side of the electronic device 100 and an additional camera (e.g., third camera) provided near the first camera 151. For example, a gap between the third camera and the first camera 151 may be realized to be greater than 30 mm and less than 80 mm. When the camera 150 further includes a third camera, the controller 110 may photograph a three-dimensional (3D) still image or 3D video by using the first camera 151 and the third camera.

The camera 150 may be realized to further include a second camera 152 on the rear side and an additional camera (e.g., fourth camera) provided near the second camera 152. For example, a gap between the fourth camera and the second camera 152 may be realized to be greater than 30 mm and less than 80 mm. When the camera 150 further includes a fourth camera, the controller 110 may photograph a 3D still image or 3D video by using the second camera 151 and the fourth camera. Further, the cameras 150 and 152 may perform a wide angle, telephoto, and macro photographing by using an additional lens attachable to an additional adapter.

The GPS 155 periodically receives signals (e.g., orbit information on the GPS satellites, time information of the satellites, and navigation messages) from a plurality of GPS satellites traveling on the orbit of the earth. In the outdoor case, the electronic device 100 may calculate positions of a plurality of GPS satellites and the electronic device 100 by using the signals provided by a plurality of GPS satellites, and may calculate a distance by using a transmitting/receiving time difference. A position, a time, or a moving speed of the electronic device 100 may be calculated through a triangulation. An additional GPS satellite may be needed for an orbit correction or a time correction.

In the indoor case when signals are received from a plurality of GPS satellites through the GPS 155, the electronic device 100 may calculate the position, the time, or the moving speed of the electronic device 100.

In the indoor case, the electronic device 100 may detect the position or the moving speed of the electronic device 100 by using a wireless AP. To detect the position of the electronic device 100 indoor, a cell-ID method using an ID of the wireless AP, an enhanced cell-ID method using an ID of the wireless AP and a received signal strength (RSS), or an angle of arrival (AoA) method using a received angle of the signal transmitted by the AP by the electronic device 100 may be used.

Further, the electronic device 100 may detect the position or the moving speed of the electronic device 100 provided indoors by using a wireless beacon (not shown). The indoor position of the electronic device 100 may be detected through various methods in addition to the above-noted method, which will be easily understood by a person skilled in the art.

The input/output unit 160 may include at least one of one or more buttons 161, a microphone 162, a speaker 163, a vibration motor 164, a connector 165, a key pad 166, and an input pen 167.

The microphone 162 receives voice or sound from the outside and generates an electrical signal by control of the controller 110. The electrical signal generated by the microphone 162 may be converted by the audio codec, may be stored in the storage unit 175, or may be output through the speaker 163 by control of the controller 110.

The speaker 163 may output sound corresponding to various signals (e.g., radio signals, broadcasting signals, audio sources, video files, or photographing) decoded by the audio codec by control of the controller 110.

The speaker 163 may output a sound (e.g., a touching sound corresponding to inputting of a telephone number, or a photographing button operating sound) corresponding to a function performed by the electronic device 100.

A plurality of speakers may be provided on a side of the electronic device 100. The electronic device 100 having a side on which an additional speaker is provided may provide a sound effect that is different from another electronic device having a front side and a rear side on which a speaker is provided.

The vibration motor 164 may convert an electrical signal to mechanical vibration by control of the controller 110. The vibration motor 164 may include a linear vibration motor, a bar type vibration motor, a coin type vibration motor, or a piezoelectric element vibration motor. For example, when a voice call request is received from another electronic device, the vibration motor 164 in the electronic device 100 in a vibration mode may be operated by control of the controller 110.

One or more vibration motors 164 may be provided on the electronic device 100. Further, the vibration motor 164 may vibrate the whole electronic device 100 or may locally vibrate part of the electronic device 100.

The connector 165 may be used as an interface for connecting the electronic device 100 and an external device or a power source. The connector 165 may be provided on one of an upper side, a lower side, and a lateral side of the electronic device 100.

The key pad 166 may receive a key input from the user so as to control the electronic device 100. The key pad 166 includes a physical key pad formed on the front of the electronic device 100, a virtual key pad displayed on an edge touch screen 190, and a physical key pad connectable in a wireless or wired manner. The physical key pad formed on the front of the electronic device 100 may be omitted depending on the performance or configuration of the electronic device 100, which will be easily understood by a person skilled in the art.

The input pen 167 may touch (or select) an object (e.g., menu, text, image, video, figure, icon, and shortcut icon) displayed (or configured) on an edge touch screen 190 of the electronic device 100 or a screen (e.g., memo screen, notepad screen, calendar screen, etc.) displayed on a writing/drawing application by the user.

The input pen 167 may touch (or select) a content (e.g., text file, image file, audio file, video file, or web page) displayed (or configured) on an edge touch screen 190 of the electronic device 100 or a screen (e.g., memo screen, note screen, calendar screen, etc.) displayed on a handwriting/drawing application by the user.

The input pen 167 may perform handwriting, drawing, painting, or sketching on a screen (e.g., memo screen, etc.) of a handwriting application or a screen (e.g., canvas screen, etc.) of a drawing application displayed on the edge touch screen 190 of the electronic device 100.

The input pen 167 may input characters by touching a capacitive, resistive, or electromagnetic resonance (EMR)

type touch screen (including an edge touch screen) or a displaying virtual key pad. The input pen 167 may include a stylus pen or a haptic pen (not shown) in which an installed vibration element (e.g., an actuator or a vibration motor) vibrates. Further, the input pen 167 may operate (e.g., may vibrate) the vibration element corresponding to sensing information detected from a sensor (e.g., an acceleration sensor, not shown) installed in the input pen 167 in addition to control information received from the electronic device 100.

When the input pen 167 is drawn out of an insertion hole, the controller 110 may perform a predetermined handwriting/drawing application to display a screen of the handwriting/drawing application on the edge touch screen 190.

The input pen 167 may include a finger (e.g., including a thumb) of a user. For example, on the application displayed on the capacitive touch screen (including a capacitive edge touch screen) or a resistive touch screen (including a resistive edge touch screen), a handwriting or a drawing may be input by the finger of a user.

When a handwriting or a drawing is input by the finger of a user on the application displayed on the capacitive edge touch screen or the resistive edge touch screen, the controller 110 may detect a touch of one of the fingers including a thumb by using the touch screen 190 and the touch screen controller 197.

It will be easily understood by a person skilled in the art that a form of the insertion hole of the electronic device 100 and/or a form (e.g., a circular cross-section or polygonal cross-section) or a structure (e.g., including a battery) of the input pen 167 may be changed depending on the performance or the structure of the electronic device 100.

The sensor unit 170 may detect a state of the electronic device 100 and/or a surrounding state of the electronic device 100. The sensor unit 170 may include one or a plurality of sensors. For example, the sensor unit 170 may include an access sensor 171 for detecting an access of the user to the electronic device 100, an illumination intensity sensor 172 for detecting an amount of light provided near the electronic device 100, or a fingerprint sensor 173 for detecting a fingerprint of the user of the electronic device 100. In addition, the sensor unit 170 may include an acceleration sensor for detecting accelerations of three axes (e.g., x-axis, y-axis, and z-axis) applied to the electronic device 100, a gravity sensor for detecting a direction in which the gravity is applied, and an altimeter for measuring a pressure in the atmosphere and detecting an altimeter.

The sensor unit 170 may respectively measure a motion acceleration and a gravity acceleration of the electronic device 100. When the electronic device 170 does not move, the sensor unit 170 may measure the gravity acceleration.

At least one sensor included in the sensor unit 170 detects a state of the electronic device 100, and generates an electrical signal corresponding to the detection and transmits the same to the controller 110. It will be easily understood by a person skilled in the art that the sensor included in the sensor unit 170 may be added, modified, or deleted depending on the performance of the electronic device 100.

The storage unit 175 may store signals and/or data that are input and/or output corresponding to the operations of the mobile communicator 120, the sub-communicator 130, the multimedia unit 140, the camera 150, the GPS 155, the input/output unit 160, the sensor unit 170, and the touch screen 190 by control of the controller 110. The storage unit 175 may store a graphical user interface (GUI) on a control program for controlling the electronic device 100 or the controller 110 and an application provided by a company or downloaded from the outside, images for providing a GUI, user information, documents, databases, or related data.

In an example embodiment, the term "storage unit" includes a storage unit 175, a ROM 112 and/or a RAM 113 provided in the controller 110, and a memory card (e.g., a micro SD card or a memory stick) installed in the electronic device 100. The storage unit may include a non-volatile memory, a volatile memory, a hard disk drive (HDD), and a solid state drive (SSD).

The power supply 180 may supply power to the constituent elements 120 through 195 provided in the electronic device 100 by control of the controller 110. The power supply 180 may supply power input from an external power source through a cable connected to the connector 165 to the respective constituent elements of the electronic device 100 by control of the controller 110. Further, the power supply 180 may supply power to one or more batteries and charge the same by control of the controller 110. The one or more batteries may be provided between the touch screen 190 provided on the front and the rear.

The power supply 180 may wirelessly charge (e.g., a magnetic resonance method, an electromagnetic wave method, or a magnetic induction method) one or more batteries by using a coil by control of the controller 110.

The edge touch screen 190 includes an edge touch panel 195 for receiving a touch input, an edge display panel 191 for displaying a screen, and an edge photo sensor 193 for receiving light with a desired (or, alternatively, a predetermined) wavelength range. The edge touch screen 190 may provide a graphical user interface (GUI) corresponding to various services (e.g., a voice call, a video call, a data transmission, receiving a broadcasting, photographing, watching a video, or performance of an application) to the user. The edge touch screen 190 may receive a single touch or a multi-touch through a body of the user (e.g., fingers including a thumb) or an input pen 167. The edge touch screen 190 transmits a signal corresponding to the single touch or the multi-touch input by the user to the edge touch screen controller 197.

Referring to FIG. 2, the edge touch screen 190 may be an integrally-formed touch screen with both lateral sides that are bent. The edge touch screen 190 may include main display regions 190a1, 190a2, and 190a3 and edge display regions 190b and 190c. The main display region 190a may be flat or may have a curvature (e.g., close to a flat state) that is less than curvatures of the edge display regions 190b and 190c.

The main display regions 190a1, 190a2, and 190a3 may be distinguished from the edge display region 190b and 190c with respect to virtual lines 190b1 and 190c1. The virtual lines 190b1 and 190c1 may mean lines where the curvatures of the main display regions 190a1, 190a2, and 190a3 start to be modified. The virtual lines 190b1 and 190c1 may mean lines where the curvatures of the main display regions 190a1, 190a2, and 190a3 are changed to the curvatures of the edge display regions 190b and 190c. The virtual lines 190b1 and 190c1 may mean lines where the curvatures of the main display regions 190a1, 190a2, and 190a3 are changed to one of the single curvature of the edge display regions 190b and 190c and a first curvature of the multi-curvature.

The curvatures of the edge display regions 190b and 190c may include one of the single curvature and the multi-curvature. Regarding the edge display regions 190b and 190c, the single curvature may mean the edge display regions 190b and 190c having one curvature. For example, the single curvature may be equal to or greater than 13R and equal to or less than 5R. Cross-sections on respective sides of the electronic device including edge display region 190*b* and 190*c* having a single curvature may include a semicircular form and an oval form.

The multi-curvature of the edge display regions 190*b* and 190*c* may mean that the first curvature corresponding to the region including virtual lines (including 190*b*1 and 190*c*1) extended from the main display regions 190*a*1, 190*a*2, and 190*a*3 and bent may be different from the second curvature corresponding to a region (e.g., including corner regions 190*b*2 and 190*c*2 of the edge display regions 190*b* and 190*c*) contacting a bezel on the front.

For example, the first curvature may be 12R or 13R. The first curvature may be equal to or greater than 13R and equal to or less than 5R. Further, the second curvature may be 6.5R or 6.9R. The second curvature may be equal to or greater than 8R and equal to or less than 4R. The cross-sections of the respective sides of the electronic device including edge display regions 190*b* and 190*c* with a multi-curvature may include a semicircular form or an oval form.

A curvature of the left edge display region 190*b* may be different from a curvature of the right edge display region 190*c*. When the edge display regions 190*b* and 190*c* have a single curvature, for example, the curvature of the left edge display region 190*b* may be 13 R. Also, the curvature of the right edge display region 190*c* may be 6.5R.

One of the edge display regions 190*b* and 190*c* may have a single curvature, and the other may have a multi-curvature. For example, the left edge display region 190*b* may have a single curvature, and the right edge display region 190*c* may have a multi-curvature. The single curvature of the left edge display region 190*b* may be 13 R, and the first curvature of the right edge display region 190*c* may be 12R and the second curvature thereof may be 6.5R.

In an example embodiment, the single curvature value and/or the multi-curvature value are examples and are not limited thereto. It will be easily understood by a person skilled in the art that the single curvature value and/or the multi-curvature value are modifiable.

The main display regions 190*a*1, 190*a*2, and 190*a*3 may be divided into a first display region 190*a*1 and second display regions 190*a*2 and 190*a*3 with respect to virtual lines 190*b*3 and 190*c*3. The virtual lines 190*b*3 and 190*c*3 may mean lines that are separated from the virtual lines 190*b*1 and 190*c*1 by a predetermined length. The second display regions 190*a*2 and 190*a*3 may mean regions that are provided near the edge display regions 190*b* and 190*c* from among the main display regions 190*a*1, 190*a*2, and 190*a*3.

The edge display panel 191 includes a plurality of pixels, and displays images through the pixels. Some of a plurality of pixels may be near infrared ray pixels for emitting light of a near infrared ray wavelength (substantially 780 nm to 1,500 nm).

For example, the edge display panel 191 may include a liquid crystal display (LCD), a light emitting diode (LED), and an organic light emitting diode (Organic LED). The edge display panel 191 may display various images and a plurality of objects according to various operational states of the electronic device 100 and executions of applications or services.

Referring back to FIG. 1, the edge photo sensor 193 is a sensor for receiving light of a desired (or, alternatively, a predetermined) wavelength, and it may include a plurality of sensor pixels that include an organic photodiode and a photo transistor. The sensor pixel may be divided into a first sensor pixel for receiving light of a near infrared ray wavelength (substantially 780 nm to 1,500 nm) and a second sensor pixel for receiving light of a red wavelength (substantially 625 nm to 740 nm).

In an example embodiment, a touch is not limited to contacts of the body of the user or the input pen 167 on the edge touch screen 190, and it includes a non-contact. For example, the non-contact may include a hovering with a gap between the edge touch screen 190 and the body of the user or the input pen 167 that is equal to or less than 50 mm. It will be easily understood by a person skilled in the art that the detectable non-contact gap on the edge touch screen 190 is modifiable according to the performance or structure of the electronic device 100.

The edge touch panel 195 may be realized to be a resistive method, a capacitive method, an infrared method, or an ultrasonic wave method.

The edge touch panel 195 may include an electromagnetic resonance (EMR) type. The electromagnetic resonance type edge touch screen further includes an additional electromagnetic resonance type edge touch panel for receiving an input of the input pen having a resonance circuit resonating in an electromagnetic resonance type loop coil.

In an example embodiment, the term "display unit" may include the edge touch screen 190.

The edge touch screen controller 197 converts an analog signal corresponding to the single touch or the multi-touch received from the edge touch panel 195 into a digital signal, and transmits the same to the controller 110. The controller 110 may calculate an X coordinate and a Y coordinate corresponding to a touching position of the touch input by the edge touch panel 195 by using the digital signal received from the edge touch screen controller 197. Further, in the case of the electromagnetic resonance type edge touch screen, an electromagnetic resonance type edge touch screen controller (not shown) may be used.

The controller 110 may control the edge touch screen 190 by using the digital signal received from the edge touch screen controller 197. For example, the controller 110 may display the shortcut icon displayed on the edge touch screen 190 corresponding to the input touch in a different manner from other shortcut icons or it may display an application screen to the edge touch screen 190 by performing an application (e.g., a telephone) corresponding to the selected shortcut icon.

The edge touch screen controller 197 may include one edge touch screen controller or a plurality of edge touch screen controllers. The edge touch screen controller 197 may be included in the controller 110 corresponding to the performance or structure of the electronic device 100. For example, in some example embodiments, the processor 111 of the controller 110 may be configured, through a layout design or execution of computer readable instructions stored in the ROM 112 and/or the RAM 113 as a special purpose computer to implement the edge touch screen controller 197.

The edge touch screen controller 197 may convert the analog signal corresponding to the touch received from the electromagnetic resonance type edge touch screen into a digital signal and may transmit the same to the controller 110, aside from the analog signal corresponding to the single touch or multi-touch received from the edge touch screen 190.

The edge touch screen controller 197 may control the red pixel and the near infrared ray pixel included in the edge display panel 191 to emit light. Further, the edge touch screen controller 197 may drive the edge photo sensor 193 to receive light around the edge touch screen 190.

After emitting the red pixel and the near infrared ray pixel included in the edge display panel 191, the edge touch screen controller 197 according to an example embodiment may analyze an optical signal acquired from a sensor pixel of the edge photo sensor 193 through blood vessels of the user to measure the heartbeat and saturation of peripheral oxygen (SpO2).

While the electronic device 100 shown in FIG. 1 and FIG. 2 shows one edge touch screen, the electronic device may include a plurality of edge touch screens. Each edge touch screen is provided in each housing (not shown), and each housing (not shown) may be mutually connected by one or a plurality of hinges (not shown).

A plurality of edge touch screens disposed from top to bottom or from right to left may be provided one a front side of one housing (not shown). A plurality of edge touch screens may be realized with an edge display panel and a plurality of edge touch panels. A plurality of edge touch screens may be realized with an edge touch panel corresponding to a plurality of edge display panels. Further, a plurality of edge touch screens may be realized with a plurality of edge touch panels corresponding to a plurality of edge display panels.

It will be easily understood by a person skilled in the art that at least one of the constituent elements of the electronic device 100 shown in FIG. 1 and FIG. 2 may be added, deleted, or modified corresponding to the performance of the electronic device 100.

A layered configuration of a region A1 of FIG. 2 will now be described with reference to FIG. 3.

Figure 3:
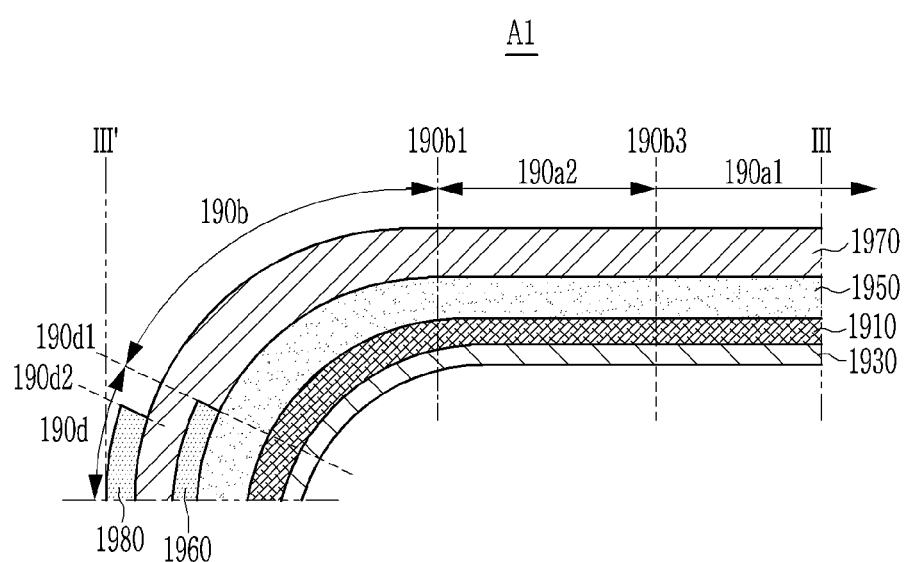
FIG. 3 shows a cross-sectional view of an edge touch screen with respect to a line III-III' of FIG. 2.

FIG. 3 shows a cross-sectional view of an edge touch screen 190 with respect to a line III-III' of FIG. 2.

Referring to FIG. 3, the edge touch screen 190 may include a display panel 1910, a sensor panel 1930, a touch panel 1950, a light blocking member 1960, a transparent protection window 1970, and a housing 1980.

The display panel 1910, the sensor panel 1930, and the touch panel 1950 are distinguished as individual layers as shown in FIG. 3. However, when the display panel 1910 is an OLED display panel, and the sensor panel 1930 includes an organic photodiode (OPD) sensor pixel, the display panel 1910 and the sensor panel 1930 may be configured to be one layer.

A plurality of pixels are provided on the display panel 1910. For example, a plurality of pixels are provided in the main display regions 190a1, 190a2, and 190a3, the edge display regions 190b and 190c, and the region 190d corresponding to the light blocking member 1960. In this instance, the near infrared ray pixel is not used for displaying an image, therefore, the near infrared ray pixel may be in a region besides the first display region 190a1 that is directly visible to the user. The near infrared ray pixel may be disposed in at least one of the second display region 190a2, the left edge display region 190b, and the region 190d corresponding to the light blocking member 1960.

The sensor panel 1930 may be provided in the region besides the first display region 190a1. For example, the sensor panel 1930 may be disposed in the second display region 190a2, the left edge display region 190b, and the region 190d corresponding to the light blocking member 1960 on a lower portion of the display panel 1910.

The sensor pixel included in the sensor panel 1930 may be disposed in at least one of the second display region 190a2, the left edge display region 190b, and the region 190d corresponding to the light blocking member 1960.

The touch panel 1950 may be integrally formed with the display panel 1910, and the touch sensor of the touch panel 1950 may be disposed on the same layer as the pixels disposed in the display panel 1910.

The light blocking member 1960 may prevent part of the display panel 1910 from being visible to the outside. A region where the display panel 1910 is blocked by the light blocking member 1960 may be wider than a region where the display panel 1910 is blocked by the housing 1980. A border line 190d1 may divide the edge display region 190b and the light blocking member 1960. A border line 190d2 may define a housing region.

While FIG. 3 illustrates the light blocking member 1960 provided on the touch panel 1950, example embodiments are not limited thereto. For example, the light blocking member 1960 may be provided on the display panel 1910.

The transparent protection window 1970 may be provided on the touch panel 1950 and the light blocking member 1960. The transparent protection window 1970 may have a shape corresponding to the curved shape of the edge touch screen 190.

A disposal of a display pixel, a near infrared ray pixel, and a sensor pixel provided in a region A1 will now be described with reference to FIG. 4 to FIG. 9.

FIG. 4 to FIG. 9 show top plan views of the region A1.

Figure 4:
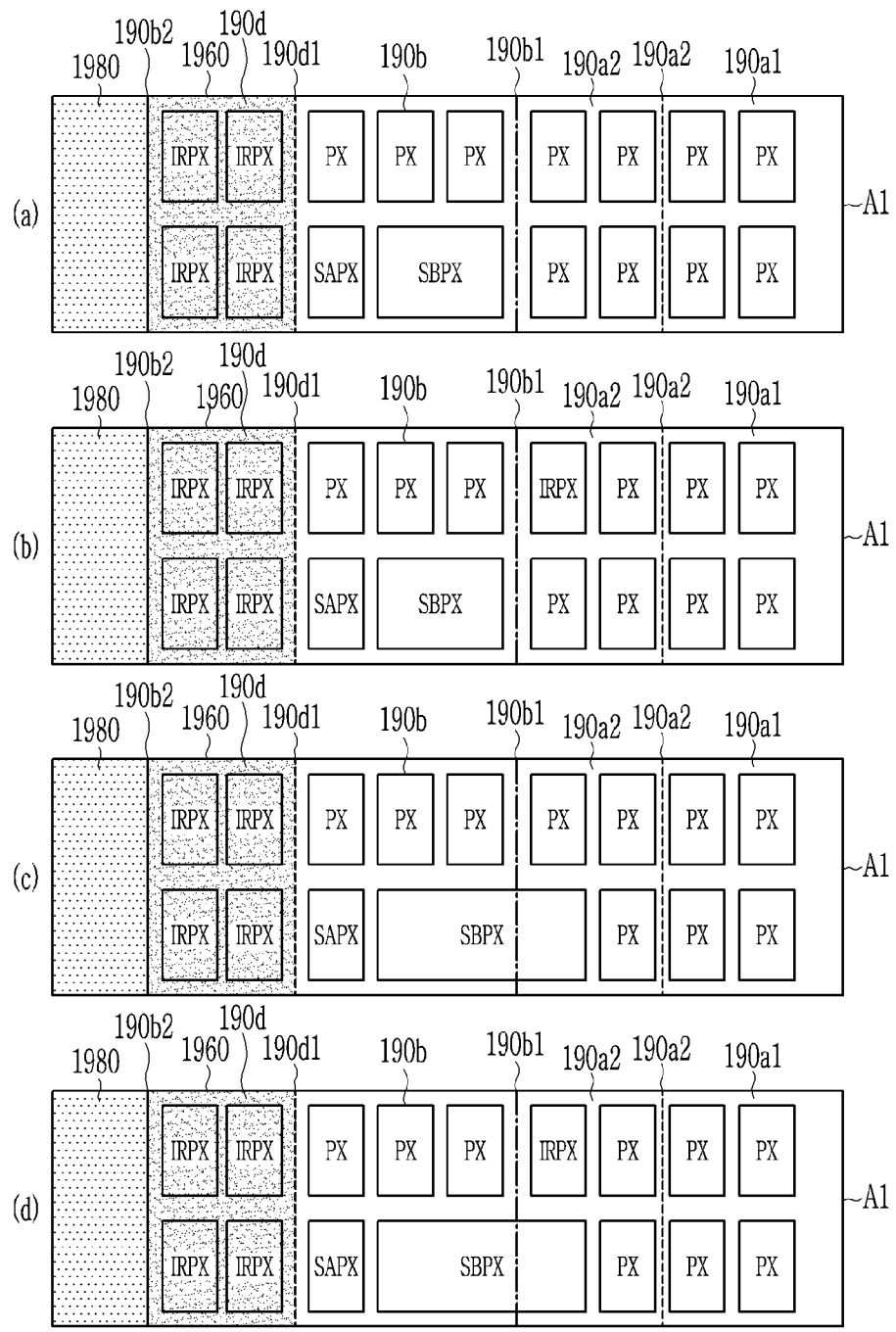
FIG. 4 to FIG. 9 show top plan views of a region A1.

FIG. 4 shows an example embodiment in which a near infrared ray pixel IRPX is provided in the region 190d corresponding to the light blocking member 1960.

As shown in graph (a) of FIG. 4, the near infrared ray pixel IRPX may be provided in the region 190d corresponding to the light blocking member 1960. The display pixel PX and the sensor pixels SAPX and SBPX may be provided in the edge display region 190b.

The first sensor pixel SAPX and the second sensor pixel SBPX may substantially have the same area, or they may have different areas as shown in graph (a) of FIG. 4.

The display pixels PXs may be provided in the main display regions 190a1 and 190a2. The display pixels PXs may emit light of a red wavelength, light of a blue wavelength, and light of a green wavelength. However, the wavelengths of light emitted by the display pixels PXs are not limited to the above description, and the display pixels PXs may emit light of the wavelength in the visible ray region.

The first sensor pixel SAPX and the second sensor pixel SBPX are shown in graph (a) of FIG. 4 to be provided on the same layer as the display pixel PX, and they are shown to not overlap the display pixel PX in a plane view, but as shown in FIG. 3, the sensor panel 1930 including a first sensor pixel SAPX and a second sensor pixel SBPX may be provided below the display panel 1910 including the display pixel PX. In this case, the first sensor pixel SAPX and the second sensor pixel SBPX may be disposed in the region not overlapping the display pixel PX.

As shown in graph (b) of FIG. 4, the near infrared ray pixel IRPX may be provided in the region 190d corresponding to the light blocking member 1960. The display pixel PX and the sensor pixels SAPX and SBPX may be provided in the edge display region 190b.

The display pixels PXs may be provided in the main display regions 190a1 and 190a2. The near infrared ray pixel IRPX may be provided in the second display region 191a2 from among the main display regions 190a1 and 190a2.

As shown in graph (c) of FIG. 4, the near infrared ray pixel IRPX may be provided in the region 190d corresponding to the light blocking member 1960. The display pixel PX and the sensor pixels SAPX and SBPX may be provided in the edge display region 190b.

The display pixel PX may be provided in the main display regions 190a1 and 190a2. The sensor pixels SAPX and SBPX may be provided in the second display region 191a2 from among the main display regions 190a1 and 190a2.

The sensor pixels SAPX and SBPX may be provided in the edge display region 190b and the second display region 191a2 for the purpose of increasing a light-receiving area of the sensor pixels SAPX and SBPX.

As shown in graph (d) of FIG. 4, the near infrared ray pixel IRPX may be provided in the region 190d corresponding to the light blocking member 1960. The display pixel PX and the sensor pixels SAPX and SBPX may be provided in the edge display region 190b.

The display pixels PXs may be provided in the main display regions 190a1 and 190a2. The near infrared ray pixel IRPX and the sensor pixels SAPX and SBPX may be provided in the second display region 191a2 from among the main display regions 190a1 and 190a2.

Figure 5:
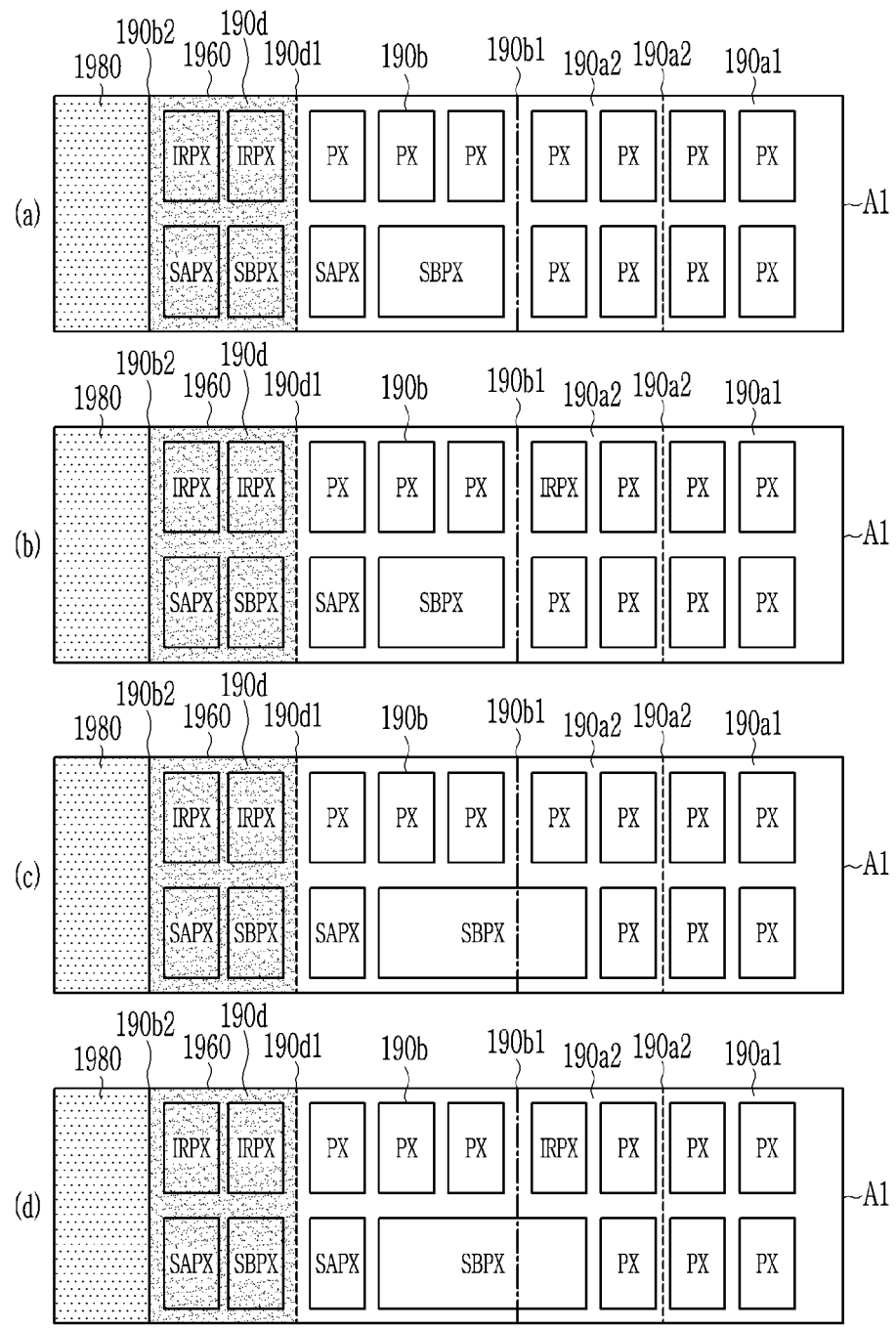

FIG. 5 shows an example embodiment in which a near infrared ray pixel IRPX and sensor pixels SAPX and SBPX are provided in the region 190d corresponding to the light blocking member 1960.

As shown in graph (a) of FIG. 5, the near infrared ray pixel IRPX and the sensor pixels SAPX and SBPX may be provided in the region 190d corresponding to the light blocking member 1960. The display pixel PX and the sensor pixels SAPX and SBPX may be provided in the edge display region 190b.

The first sensor pixel SAPX and the second sensor pixel SBPX may substantially have the same area, or they may have different areas as shown in graph (a) of FIG. 5.

The display pixels PXs may be provided in the main display regions 190a1 and 190a2. The display pixels PXs may respectively emit light of the red wavelength, light of the blue wavelength, and light of the green wavelength. However, the wavelength of light emitted by the display pixels PXs are not limited to the above description, and the display pixels PXs may emit light of the wavelength in the visible ray region.

The first sensor pixel SAPX and the second sensor pixel SBPX are shown to be provided on the same layer as the display pixel PX and are shown to not overlap the display pixel PX in a plane view in graph (a) of FIG. 5, but as shown in FIG. 3, the sensor panel 1930 including the first sensor pixel SAPX and the second sensor pixel SBPX may be provided below the display panel 1910 including the display pixel PX. In this case, the first sensor pixel SAPX and the second sensor pixel SBPX may be disposed in the region that does not overlap the display pixel PX in a plane view.

As shown in graph (b) of FIG. 5, the near infrared ray pixel IRPX and the sensor pixels SAPX and SBPX may be provided in the region 190d corresponding to the light blocking member 1960. The display pixel PX and the sensor pixels SAPX and SBPX may be provided in the edge display region 190b.

The display pixels PXs may be provided in the main display regions 190a1 and 190a2. The near infrared ray pixel IRPX may be provided in the second display region 191a2 from among the main display regions 190a1 and 190a2.

As shown in graph (c) of FIG. 5, the near infrared ray pixel IRPX and the sensor pixels SAPX and SBPX may be provided in the region 190d corresponding to the light blocking member 1960. The display pixel PX and the sensor pixels SAPX and SBPX may be provided in the edge display region 190b.

The display pixels PXs may be provided in the main display regions 190a1 and 190a2. The sensor pixels SAPX and SBPX may be provided in the second display region 191a2 from among the main display regions 190a1 and 190a2.

Some sensor pixels SAPX and SBPX may be provided on the edge display region 190b and the second display region 191a2 for the purpose of increasing the light receiving area of the sensor pixels SAPX and SBPX.

As shown in graph (d) of FIG. 5, the near infrared ray pixel IRPX and the sensor pixels SAPX and SBPX may be provided in the region 190d corresponding to the light blocking member 1960. The display pixel PX and the sensor pixels SAPX and SBPX may be provided in the edge display region 190b.

The display pixels PXs may be provided in the main display regions 190a1 and 190a2. The near infrared ray pixel IRPX and the sensor pixels SAPX and SBPX may be provided in the second display region 191a2 from among the main display regions 190a1 and 190a2.

Figure 6:
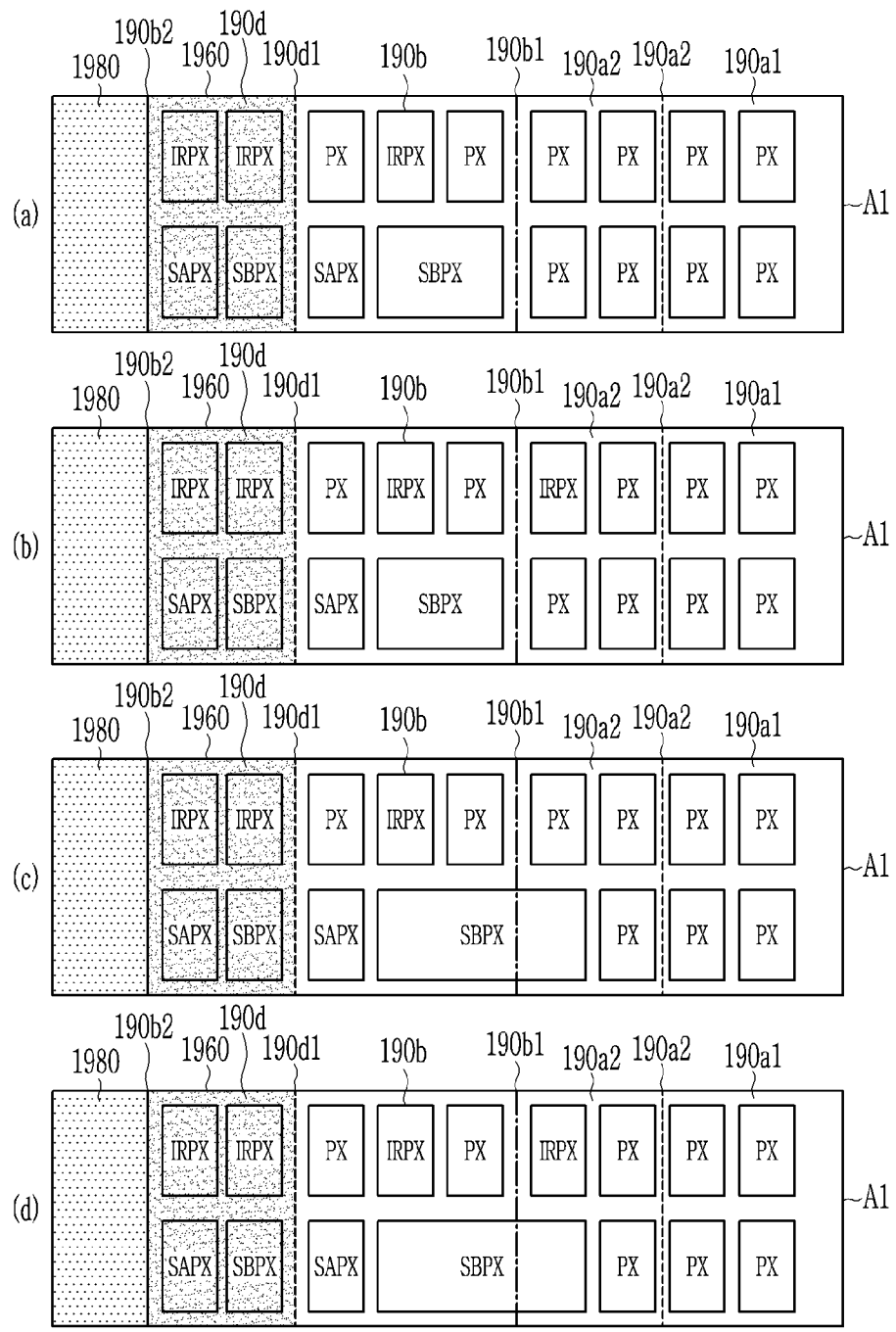

FIG. 6 shows an example embodiment in which the near infrared ray pixel IRPX and the sensor pixels SAPX and SBPX are provided in the region 190d of the light blocking member 1960, and the display pixel PX, the near infrared ray pixel IRPX, and the sensor pixels SAPX and SBPX are provided in the edge display region 190b.

As shown in graph (a) of FIG. 6, the near infrared ray pixel IRPX and the sensor pixels SAPX and SBPX may be provided in the region 190d corresponding to the light blocking member 1960. The display pixel PX, the near infrared ray pixel IRPX, and the sensor pixels SAPX and SBPX may be provided in the edge display region 190b.

The first sensor pixel SAPX and the second sensor pixel SBPX may substantially have the same area with each other, or they may have different areas as shown in graph (a) of FIG. 6.

The display pixels PXs may be provided in the main display regions 190a1 and 190a2. The display pixels PXs may respectively emit light of the red wavelength, light of the blue wavelength, and light of the green wavelength. However, the wavelength of light emitted by the display pixels PXs are not limited to the above description, and the display pixels PXs may emit light of the wavelength in the visible ray region.

The first sensor pixel SAPX and the second sensor pixel SBPX are shown to be provided on the same layer as the display pixel PX and are shown to not overlap the display pixel PX in a plane view in graph (a) of FIG. 6, but as shown in FIG. 3, the sensor panel 1930 including the first sensor pixel SAPX and the second sensor pixel SBPX may be provided below the display panel 1910 including the display pixel PX. In this case, the first sensor pixel SAPX and the second sensor pixel SBPX may be disposed in the region that does not overlap the display pixel PX in a plane view.

As shown in graph (b) of FIG. 6, the near infrared ray pixel IRPX and the sensor pixels SAPX and SBPX may be provided in the region 190d corresponding to the light blocking member 1960. The display pixel PX, the near infrared ray pixel IRPX, and the sensor pixels SAPX and SBPX may be provided in the edge display region 190b.

The display pixels PX may be provided in the main display regions 190a1 and 190a2. The near infrared ray pixel IRPX may be provided in the second display region 191a2 from among the main display regions 190a1 and 190a2.

As shown in graph (c) of FIG. 6, the near infrared ray pixel IRPX and the sensor pixels SAPX and SBPX may be provided in the region 190*d* corresponding to the light blocking member 1960. The display pixel PX, the near infrared ray pixel IRPX, and the sensor pixels SAPX and SBPX may be provided in the edge display region 190*b*.

The display pixels PXs may be provided in the main display regions 190*a*1 and 190*a*2. The sensor pixels SAPX and SBPX may be provided in the second display region 191*a*2 from among the main display regions 190*a*1 and 190*a*2.

Some sensor pixels SAPX and SBPX may be provided on the edge display region 190*b* and the second display region 191*a*2 for the purpose of increasing the light receiving area of the sensor pixels SAPX and SBPX.

As shown in graph (d) of FIG. 6, the near infrared ray pixel IRPX and the sensor pixels SAPX and SBPX may be provided in the region 190*d* corresponding to the light blocking member 1960. The display pixel PX, the near infrared ray pixel IRPX, and the sensor pixels SAPX and SBPX may be provided in the edge display region 190*b*.

The display pixels PXs may be provided in the main display regions 190*a*1 and 190*a*2. The near infrared ray pixel IRPX and the sensor pixels SAPX and SBPX may be provided in the second display region 191*a*2 from among the main display regions 190*a*1 and 190*a*2.

Figure 7:
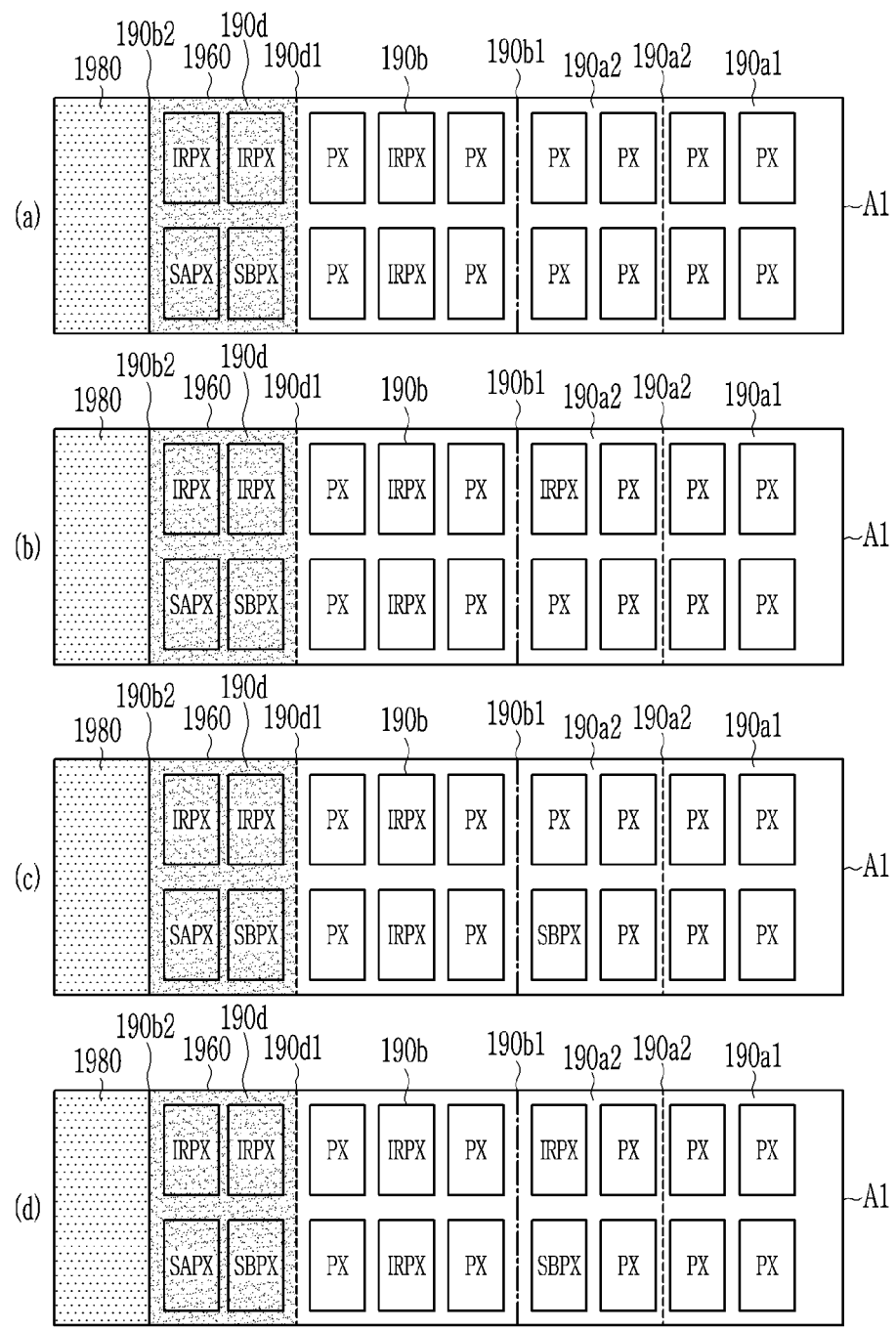

FIG. 7 shows an example embodiment in which the near infrared ray pixel IRPX and the sensor pixels SAPX and SBPX are provided in the region 190*d* corresponding to the light blocking member 1960, and the display pixel PX and the near infrared ray pixel IRPX are provided in the edge display region 190*b*.

As shown in graph (a) of FIG. 7, the near infrared ray pixel IRPX and the sensor pixels SAPX and SBPX may be provided in the region 190*d* corresponding to the light blocking member 1960. The display pixel PX and the near infrared ray pixel IRPX may be provided in the edge display region 190*b*.

The first sensor pixel SAPX and the second sensor pixel SBPX may substantially have the same area with each other, or they may have different areas as shown in graph (a) of FIG. 7.

The display pixels PXs may be provided in the main display regions 190*a*1 and 190*a*2. The display pixels PXs may respectively emit light of the red wavelength, light of the blue wavelength, and light of the green wavelength. However, the wavelength of light emitted by the display pixels PXs are not limited to the above description, and the display pixels PXs may emit light of the wavelength in the visible ray region.

The first sensor pixel SAPX and the second sensor pixel SBPX are shown to be provided on the same layer as the display pixel PX and are shown to not overlap the display pixel PX in a plane view in graph (a) of FIG. 7, but as shown in FIG. 3, the sensor panel 1930 including the first sensor pixel SAPX and the second sensor pixel SBPX may be provided below the display panel 1910 including the display pixel PX. In this case, the first sensor pixel SAPX and the second sensor pixel SBPX may be disposed in the region that does not overlap the display pixel PX in a plane view.

As shown in graph (b) of FIG. 7, the near infrared ray pixel IRPX and the sensor pixels SAPX and SBPX may be provided in the region 190*d* corresponding to the light blocking member 1960. The display pixel PX and the near infrared ray pixel IRPX may be provided in the edge display region 190*b*.

The display pixels PX may be provided in the main display regions 190*a*1 and 190*a*2. The near infrared ray pixel IRPX may be provided in the second display region 191*a*2 from among the main display regions 190*a*1 and 190*a*2.

As shown in graph (c) of FIG. 7, the near infrared ray pixel IRPX and the sensor pixels SAPX and SBPX may be provided in the region 190*d* corresponding to the light blocking member 1960. The display pixel PX and the near infrared ray pixel IRPX may be provided in the edge display region 190*b*.

The display pixels PXs may be provided in the main display regions 190*a*1 and 190*a*2. The near infrared ray pixel IRPX may be provided in the second display region 191*a*2 from among the main display regions 190*a*1 and 190*a*2.

As shown in graph (d) of FIG. 7, the near infrared ray pixel IRPX and the sensor pixels SAPX and SBPX may be provided in the region 190*d* corresponding to the light blocking member 1960. The display pixel PX and the near infrared ray pixel IRPX may be provided in the edge display region 190*b*.

The display pixels PXs may be provided in the main display regions 190*a*1 and 190*a*2. The near infrared ray pixel IRPX and the sensor pixels SAPX and SBPX may be provided in the second display region 191*a*2 from among the main display regions 190*a*1 and 190*a*2.

Figure 8:
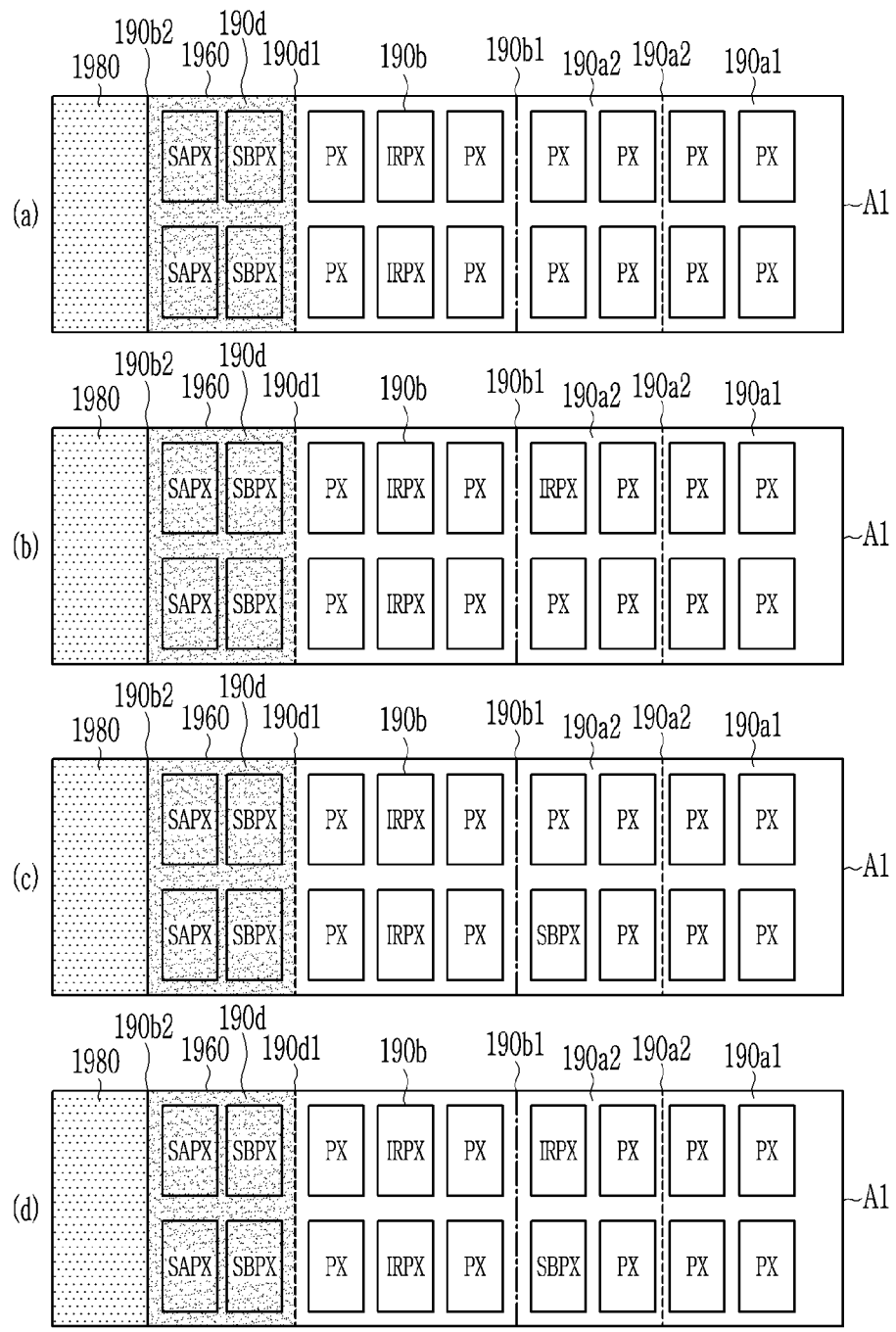

FIG. 8 shows an example embodiment in which the sensor pixels SAPX and SBPX are provided in the region 190*d* corresponding to the light blocking member 1960.

As shown in graph (a) of FIG. 8, the sensor pixels SAPX and SBPX may be provided in the region 190*d* corresponding to the light blocking member 1960. The display pixel PX and the near infrared ray pixel IRPX may be provided in the edge display region 190*b*.

The first sensor pixel SAPX and the second sensor pixel SBPX may substantially have the same area with each other as shown in graph (a) of FIG. 8, or they may have different areas.

The display pixels PXs may be provided in the main display regions 190*a*1 and 190*a*2. The display pixels PXs may respectively emit light of the red wavelength, light of the blue wavelength, and light of the green wavelength. However, the wavelength of light emitted by the display pixels PXs are not limited to the above description, and the display pixels PXs may emit light of the wavelength in the visible ray region.

The near infrared ray pixel IRPX may be provided in the second display region 191*a*2 from among the main display regions 190*a*1 and 190*a*2.

The first sensor pixel SAPX and the second sensor pixel SBPX are shown to be provided on the same layer as the display pixel PX and are shown to not overlap the display pixel PX in a plane view in graph (a) of FIG. 8, but as shown in FIG. 3, the sensor panel 1930 including the first sensor pixel SAPX and the second sensor pixel SBPX may be provided below the display panel 1910 including the display pixel PX. In this case, the first sensor pixel SAPX and the second sensor pixel SBPX may be disposed in the region that does not overlap the display pixel PX in a plane view.

As shown in graph (b) of FIG. 8, the sensor pixels SAPX and SBPX may be provided in the region 190*d* corresponding to the light blocking member 1960. The display pixel PX and the near infrared ray pixel IRPX may be provided in the edge display region 190*b*.

The display pixels PXs may be provided in the main display regions 190*a*1 and 190*a*2. The near infrared ray pixel IRPX may be provided in the second display region 191*a*2 from among the main display regions 190*a*1 and 190*a*2.

As shown in graph (c) of FIG. 8, the sensor pixels SAPX and SBPX may be provided in the region 190*d* corresponding to the light blocking member 1960. The display pixel PX and the near infrared ray pixel IRPX may be provided in the edge display region 190*b*.

The display pixels PXs may be provided in the main display regions 190*a*1 and 190*a*2. The sensor pixels SAPX and SBPX may be provided in the second display region 191*a*2 from among the main display regions 190*a*1 and 190*a*2.

As shown in graph (d) of FIG. 8, the sensor pixels SAPX and SBPX may be provided in the region 190*d* corresponding to the light blocking member 1960. The display pixel PX and the near infrared ray pixel IRPX may be provided in the edge display region 190*b*.

The display pixels PXs may be provided in the main display regions 190*a*1 and 190*a*2. The near infrared ray pixel IRPX and the sensor pixels SAPX and SBPX may be provided in the second display region 191*a*2 from among the main display regions 190*a*1 and 190*a*2.

Figure 9:
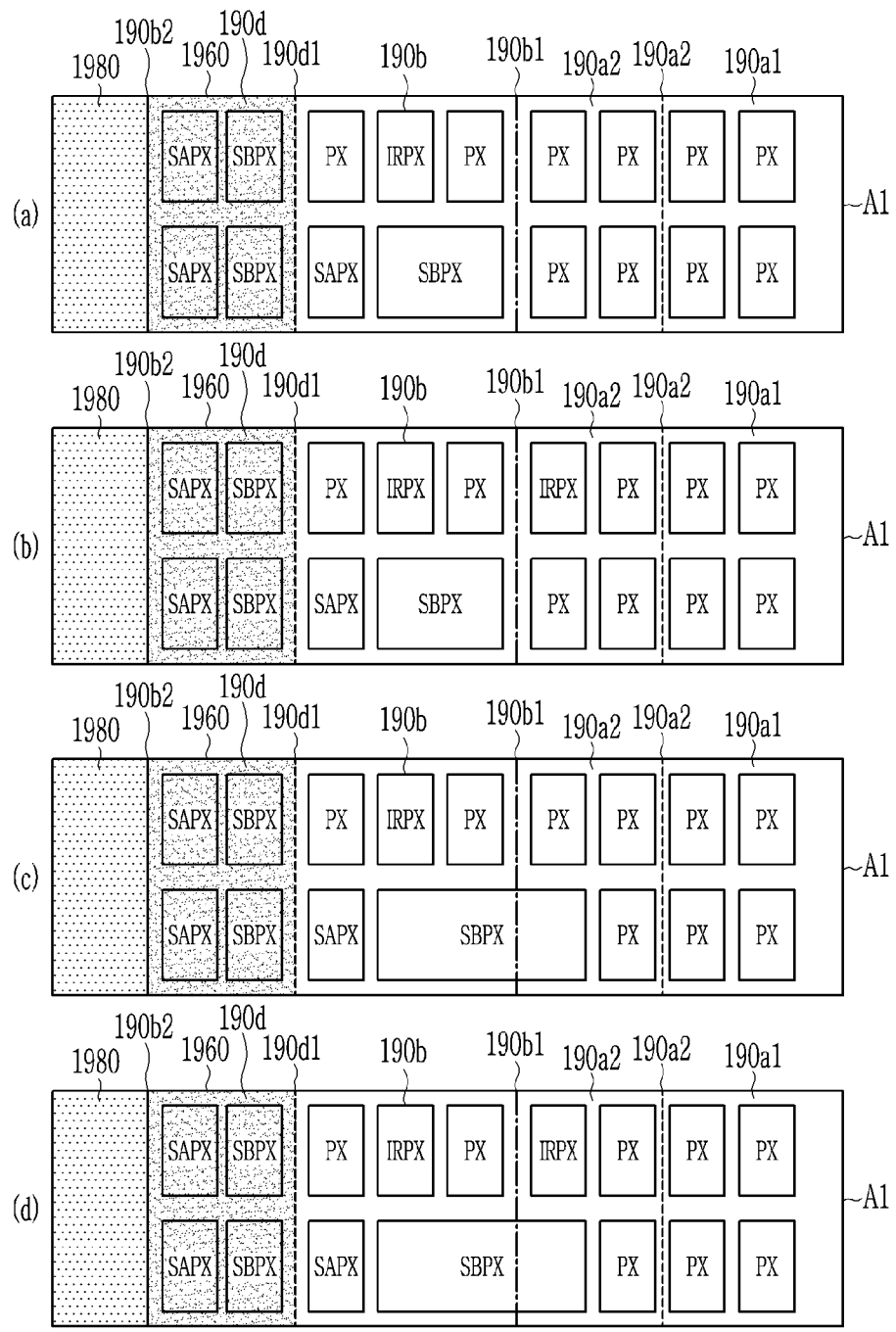

FIG. 9 shows an example embodiment in which the sensor pixels SAPX and SBPX are provided in the region 190*d* corresponding to the light blocking member 1960.

As shown in graph (a) of FIG. 9, the sensor pixels SAPX and SBPX may be provided in the region 190*d* corresponding to the light blocking member 1960. The display pixel PX, the near infrared ray pixel IRPX, and the sensor pixels SAPX and SBPX may be provided in the edge display region 190*b*.

The first sensor pixel SAPX and the second sensor pixel SBPX may substantially have the same area with each other, or they may have different areas as shown in graph (a) of FIG. 9.

The display pixels PXs may be provided in the main display regions 190*a*1 and 190*a*2. The display pixels PXs may respectively emit light of the red wavelength, light of the blue wavelength, and light of the green wavelength. However, the wavelength of light emitted by the display pixels PXs are not limited to the above description, and the display pixels PXs may emit light of the wavelength in the visible ray region.

The first sensor pixel SAPX and the second sensor pixel SBPX are shown to be provided on the same layer as the display pixel PX and are shown to not overlap the display pixel PX in a plane view in graph (a) of FIG. 9, but as shown in FIG. 3, the sensor panel 1930 including the first sensor pixel SAPX and the second sensor pixel SBPX may be provided below the display panel 1910 including the display pixel PX. In this case, the first sensor pixel SAPX and the second sensor pixel SBPX may be disposed in the region that does not overlap the display pixel PX in a plane view.

As shown in graph (b) of FIG. 9, the sensor pixels SAPX and SBPX may be provided in the region 190*d* corresponding to the light blocking member 1960. The display pixel PX, the near infrared ray pixel IRPX, and the sensor pixels SAPX and SBPX may be provided in the edge display region 190*b*.

The display pixels PXs may be provided in the main display regions 190*a*1 and 190*a*2. The near infrared ray pixel IRPX may be provided in the second display region 191*a*2 from among the main display regions 190*a*1 and 190*a*2.

As shown in graph (c) of FIG. 9, the sensor pixels SAPX and SBPX may be provided in the region 190*d* corresponding to the light blocking member 1960. The display pixel PX, the near infrared ray pixel IRPX, and the sensor pixels SAPX and SBPX may be provided in the edge display region 190*b*.

The display pixels PXs may be provided in the main display regions 190*a*1 and 190*a*2. The sensor pixels SAPX and SBPX may be provided in the second display region 191*a*2 from among the main display regions 190*a*1 and 190*a*2.

Some sensor pixels SAPX and SBPX may be provided on the edge display region 190*b* and the second display region 191*a*2 for the purpose of increasing the light receiving area of the sensor pixels SAPX and SBPX.

As shown in graph (d) of FIG. 9, the sensor pixels SAPX and SBPX may be provided in the region 190*d* corresponding to the light blocking member 1960. The display pixel PX, the near infrared ray pixel IRPX, and the sensor pixels SAPX and SBPX may be provided in the edge display region 190*b*.

The display pixels PXs may be provided in the main display regions 190*a*1 and 190*a*2. The near infrared ray pixel IRPX and the sensor pixels SAPX and SBPX may be provided in the second display region 191*a*2 from among the main display regions 190*a*1 and 190*a*2.

A method for controlling an electronic device 100 for measuring a heartbeat and/or a saturation of peripheral oxygen (SpO2) of a user by using the above-configured edge touch screen will now be described with reference to FIG. 10 and FIG. 11.

Figure 10:
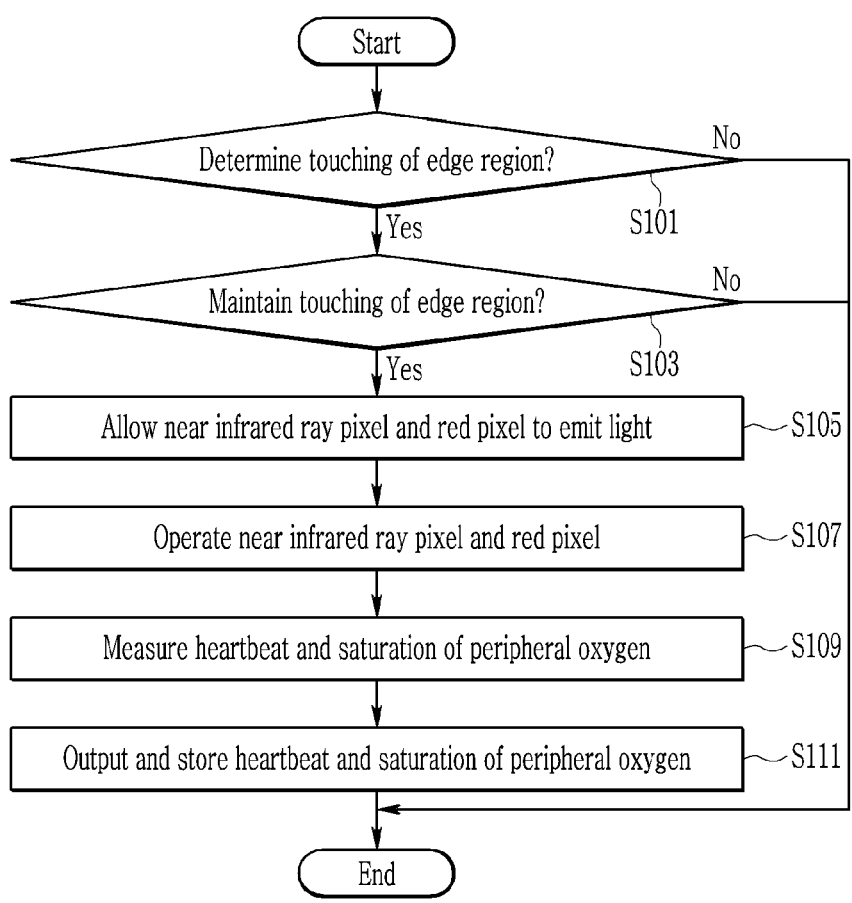
FIG. 10 shows a flowchart of a method for controlling an electronic device according to an example embodiment.

FIG. 10 shows a flowchart of a method for controlling an electronic device 100 according to an example embodiment.

Referring to FIG. 10, in operation S101, the controller 110 determines whether a touch input of the user of the edge touch screen 190 is sensed in the edge display regions 190*b* and 190*c*.

For example, when the user grasps the electronic device 100, the finger of the user may contact the edge display regions 190*b* and 190*c* of the edge touch screen 190. The touch sensor of the edge display regions 190*b* and 190*c* of the edge touch panel 195 detects the touch, and transmits a corresponding signal to the edge touch screen controller 197. The edge touch screen controller 197 transmits the touch signal provided by the edge touch panel 195 to the controller 110. When the touch signal is input, the controller 110 determines as that the touch input of the user is sensed. In other example embodiments, the edge touch screen controller 197 and the controller 110 may be embodied in the same controller such that the touch sensor transmits the corresponding signal directly to the controller 110.

In operation S103, the controller 110 may determine whether the touch input of the user in the edge display regions 190*b* and 190*c* is maintained. The controller 110 may determine whether the touch input of the user in the edge display regions 190*b* and 190*c* is maintained for a desired (or, alternatively, a predetermined) time (e.g., one second).

For example, the controller 110 may not start or may stop measuring of a heartbeat and/or a saturation of peripheral oxygen (SpO2) when a touch input of the user of the edge touch screen 190 is not provided or the touch input of the user in the edge display regions 190*b* and 190*c* is not maintained.

In contrast, when the finger of the user contacts the edge display regions 190*b* and 190*c* for one second as the user grasps the electronic device 100, the controller 110 may determine as that the touch input of the user is maintained and proceed to operation S105.

In operation S105, when the touch input of the user in the edge display regions 190b and 190c is maintained, the controller 110 instructs the near infrared ray pixel IRPX and the red pixel corresponding to the region on the edge display panel 1910 touched by the user to emit light. The controller 110 calculates a touch position of the touch input provided to the edge touch panel 195 and maintained.

For example, when the near infrared ray pixels IRPXs are provided in the edge display regions 190b and 190c, the controller 110 may instruct the near infrared ray pixels IRPXs provided near the touch position and provided in the edge display regions 190b and 190c to emit light. Further, when the near infrared ray pixels IRPXs are provided in the region 190d corresponding to the light blocking member 1960, the controller 110 may instruct the near infrared ray pixel IRPX provided in a row provided near the touch position and provided in the region 190d corresponding to the light blocking member 1960 to emit light. Also, when the near infrared ray pixels IRPXs are provided in the edge second display region 191a2, the controller 110 may instruct the near infrared ray pixel IRPX provided in a row provided near the touch position and provided in the second display region 191a2 to emit light. In addition, the controller 110 may combine the above-described example embodiments and instruct the near infrared ray pixel IRPX to emit light according to the position of the near infrared ray pixels IRPXs.

For example, when the red pixels are provided in the edge display regions 190b and 190c, the controller 110 may instruct the red pixels provided near the touch position and provided in the edge display region 190b and 190c to emit light. Further, when the red pixels are provided in the edge second display region 191a2, the controller 110 may instruct the red pixel provided near the touch position and provided in the second display region 191a2 to emit light. In addition, the controller 110 may combine the example embodiments and may instruct the red pixels to emit light according to the position of the red pixels.

Further, in addition to emitting light when the touch input of the user is determined to be maintained, the controller 110 may also notify the user of starting of measuring a heartbeat and/or a saturation of peripheral oxygen (SpO2) through an output unit 160 such as the edge touch screen 190, the speaker 163, and/or the vibration motor 164.

In addition, when the touch input of the user is determined to be maintained, the controller 110 may display an alert window for inquiring a start of measuring a heartbeat and/or a saturation of peripheral oxygen (SpO2) to the edge touch screen 190, and may receive a measurement start command or a measurement stop command from the user.

In operation S107, the controller 110 operates the near infrared ray sensor pixels SAPX and SBPX and the red sensor pixels SAPX and SBPX corresponding to the region touched by the user to receive information from the near infrared ray sensor pixels SAPX and SBPX and the red sensor pixels SAPX and SBPX. In some example embodiments, the information may be associated with an amount of reflected light received by the near infrared ray sensor pixels SAPX and SBPX and the red sensor pixels SAPX and SBPX.

For example, when the near infrared ray sensor pixels SAPX and SBPX and the red sensor pixels SAPX and SBPX are provided in the edge display regions 190b and 190c, the controller 110 may operate the near infrared ray sensor pixels SAPX and SBPX and the red sensor pixels SAPX and SBPX provided near the touch position and provided in the edge display region 190b and 190c. When the near infrared ray sensor pixels SAPX and SBPX and the red sensor pixels SAPX and SBPX are provided in the region 190d corresponding to the light blocking member 1960, the controller 110 may operate the near infrared ray sensor pixels SAPX and SBPX and the red sensor pixels SAPX and SBPX provided in a row provided near the touch position and provided in the region 190d corresponding to the light blocking member 1960. When the near infrared ray sensor pixels SAPX and SBPX and the red sensor pixels SAPX and SBPX are provided in the edge second display region 191a2, the controller 110 may operate the near infrared ray sensor pixels SAPX and SBPX and the red sensor pixels SAPX and SBPX provided in a row provided near the touch position and provided in the second display region 191a2. Besides this, the controller 110 may combine the example embodiments and may operate the sensor pixels SAPX and SBPX according to the position of the sensor pixels SAPX and SBPX.

In operation S109, the controller 110 measures a heartbeat and/or a saturation of peripheral oxygen (SpO2) of the user by using a change of an amount of light received by the near infrared ray sensor pixels SAPX and SBPX and the red sensor pixels SAPX and SBPX.

The heartbeat may be measured by converting a blood flow change that is a volume change of peripheral blood vessels into a light amount change. The saturation of peripheral oxygen (SpO2) represents biometrics for indicating a content of oxygen that exists in the hemoglobin from among various components of the blood, and it may be measured by sequentially emitting the red light and the near infrared ray light through the red pixel and the near infrared ray pixel IRPX for each period to irradiate the same to a peripheral blood vessel part (e.g., a finger end) of the user, allowing the same to be reflected on the human body, receiving light by the near infrared ray sensor pixels SAPX and SBPX and the red sensor pixels SAPX and SBPX, and observing the change of the amount of the received light. A method for measuring a heartbeat and a saturation of peripheral oxygen (SpO2) using near infrared ray light and red light is known to a person skilled in the art, so no description thereof will be provided.

In operation S111, the controller 110 outputs heartbeat and saturation of peripheral oxygen (SpO2) information to the edge touch screen 190 and/or the speaker 163, and stores the same in the storage unit 175.

The controller 110 may display heartbeat and saturation of peripheral oxygen (SpO2) information using the edge touch screen 190, and/or may output the heartbeat and saturation of peripheral oxygen (SpO2) information as a voice through the speaker 163.

Further, the controller 110 may store the heartbeat and saturation of peripheral oxygen (SpO2) information in the storage unit 175, and the user may check his health state in a later time.

In addition, the controller 110 may report the heartbeat and saturation of peripheral oxygen (SpO2) information to an external storage unit or a server through the mobile communicator 120 and the sub-communicator 130.

According to at least one of the example embodiments, the biometrics of the user may be conveniently measured without an additional module, so the inner space of the electronic device 100 may be efficiently used. Hence, the electronic device 100 may become slim or down-sized, and the effect of providing a new user experience to the user is generated.

Figure 11:
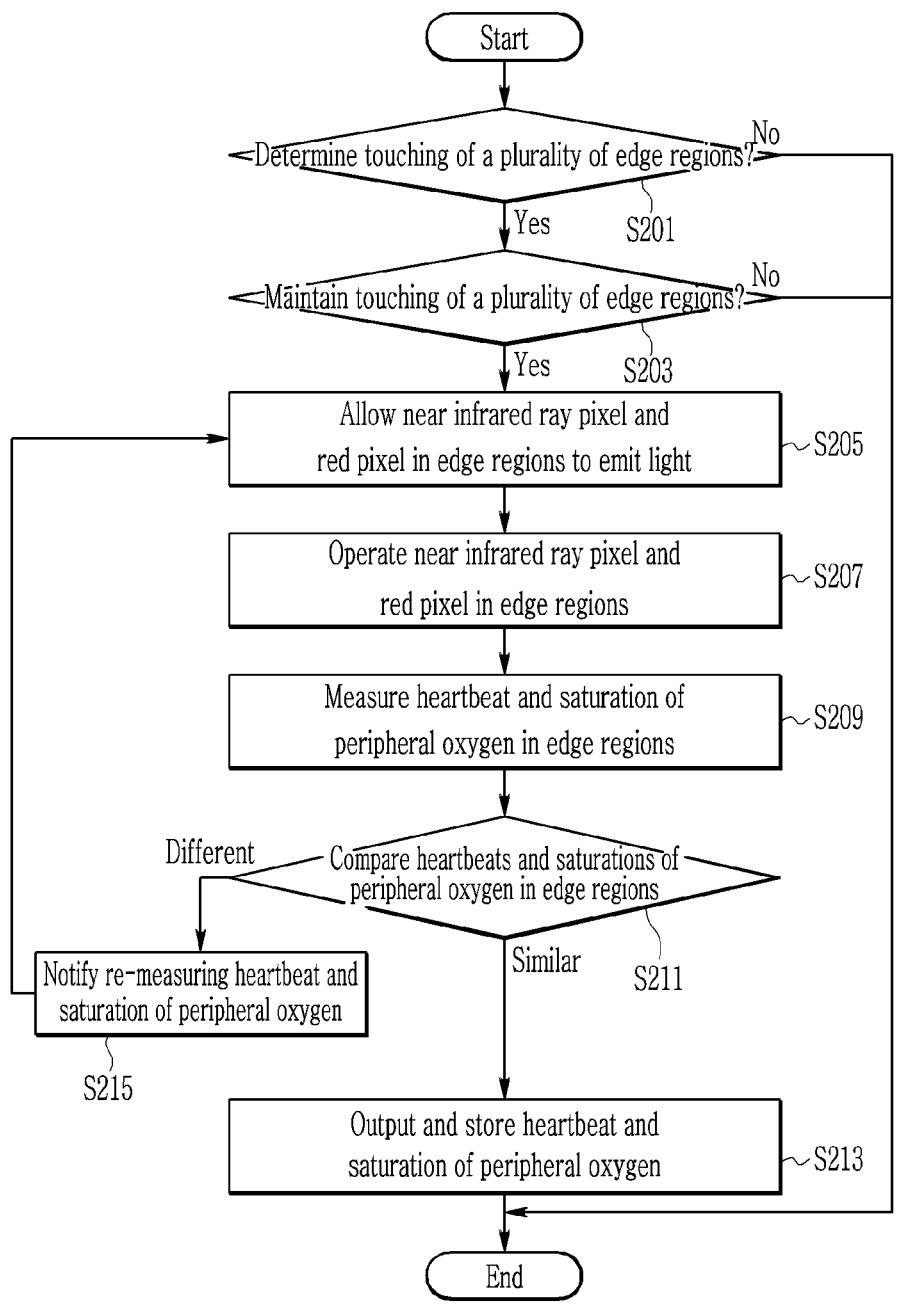
FIG. 11 shows a flowchart of a method for controlling another electronic device according to an example embodiment.

FIG. 11 shows a flowchart of a method for an electronic device 100 according to another example embodiment.

Referring to FIG. 11, in operation S201, the controller 110 determines whether the touch input of the user of the edge touch screen 190 is sensed in a plurality of regions in the edge display regions 190b and 190c.

For example, when the user grasps the electronic device 100, the finger of the user may contact the left edge display region 190b and the right edge display region 190c of the edge touch screen 190. Respective touch sensors of the left edge display region 190b and the right edge display region 190c of the edge touch panel 195 may detect the touch, and transmit a corresponding signal to the edge touch screen controller 197. The edge touch screen controller 197 transmits the touch signal detected by the left edge display region 190b and the touch signal detected by the right edge display region 190c to the controller 110. When the touch signals corresponding to the touch in the left edge display region 190b and the touch in the right edge display region 190c, that is, the multi-touch in the respective edge display regions 190b and 190c are input, the controller 110 determines as that the touch input of the user is sensed in a plurality of regions in the edge display regions 190b and 190c.

In operation S203, the controller 110 determines whether the touch input of the user in a plurality of regions in the edge display regions 190b and 190c is maintained. The controller 110 may determine whether the touch input of the user in a plurality of regions in the edge display regions 190b and 190c are maintained for a desired (or, alternatively, a predetermined) time (e.g., one second).

For example, when the finger of the user contacts a plurality of regions in the edge display region 190b and 190c for one second in order for the user to grasp the electronic device 100, the controller 110 may determine as that the touch input of the user is maintained.

When the touch input of the user on the edge touch screen 190 is not provided or the touch input of the user in the edge display regions 190b and 190c is not maintained, the controller 110 does not start measuring the heartbeat and the saturation of peripheral oxygen (SpO2) or stops the same.

In operation S205, when the touch input of the user in a plurality of regions in the edge display regions 190b and 190c is maintained, the controller 110 instructs the near infrared ray pixel IRPX and the red pixel to emit light corresponding to the region touched by the user. For example, the controller 110 calculates a touch position of the touch input provided to the edge touch panel 195 and maintained. The controller 110 instructs the near infrared ray pixel IRPX and the red pixel of the touch input on the edge display panel 1910 to emit light.

For example, when the near infrared ray pixels IRPXs are provided in the edge display regions 190b and 190c, the controller 110 may instruct the near infrared ray pixels IRPXs provided near the touch position and provided in the edge display regions 190b and 190c to emit light. Also, the near infrared ray pixels IRPXs are provided in the region 190d corresponding to the light blocking member 1960, the controller 110 may instruct the near infrared ray pixel IRPX provided in the row provided near the touch position and provided in the region 190d corresponding to the light blocking member 1960 to emit light. Further, when the near infrared ray pixels IRPXs are provided in the edge second display region 191a2, the controller 110 may instruct the near infrared ray pixel IRPX provided in the row provided near the touch position and provided in the second display region 191a2 to emit light. In addition, the controller 110 may combine the example embodiments and instruct the near infrared ray pixel IRPX to emit light according to the position of the near infrared ray pixels IRPXs.

For example, when the red pixels are provided in the edge display regions 190b and 190c, the controller 110 may instruct the red pixels provided near the touch position and provided in the edge display regions 190b and 190c to emit light. Also, when the red pixels are provided in the edge second display region 191a2, the controller 110 may instruct the red pixel provided in the row provided near the touch position and provided in the second display region 191a2 to emit light. In addition, the controller 110 may combine the example embodiments and may instruct the red pixels to emit light according to the position of the red pixels.

When the touch input is determined to be maintained, the controller 110 may notify the user of starting of a measurement of the heartbeat and/or the saturation of peripheral oxygen (SpO2) through the output unit 160 such as the edge touch screen 190, the speaker 163, and/or the vibration motor 164.

In addition, when the touch input of the user is determined to be maintained, the controller 110 may display an alert window for inquiring a starting of measurement of the heartbeat and the saturation of peripheral oxygen (SpO2) to the edge touch screen 190, and may receive a measurement start command or a measurement stop command.

In operation S207, the controller 110 operates the near infrared ray sensor pixels SAPX and SBPX and the red sensor pixels SAPX and SBPX corresponding to the region touched by the user to receive information from the near infrared ray sensor pixels SAPX and SBPX and the red sensor pixels SAPX and SBPX. In some example embodiments, the information may be associated with an amount of reflected light received by the near infrared ray sensor pixels SAPX and SBPX and the red sensor pixels SAPX and SBPX.

For example, when the near infrared ray sensor pixels SAPX and SBPX and the red sensor pixels SAPX and SBPX are provided in the edge display regions 190b and 190c, the controller 110 may operate the near infrared ray sensor pixels SAPX and SBPX and the red sensor pixels SAPX and SBPX provided near the touch position and provided in the edge display regions 190b and 190c. When the near infrared ray sensor pixels SAPX and SBPX and the red sensor pixels SAPX and SBPX are provided in the region 190d corresponding to the light blocking member 1960, the controller 110 may operate the near infrared ray sensor pixels SAPX and SBPX and the red sensor pixels SAPX and SBPX provided in the row provided near the touch position and provided in the region 190d corresponding to the light blocking member 1960. When the near infrared ray sensor pixels SAPX and SBPX and the red sensor pixels SAPX and SBPX are provided in the edge second display region 191a2, the controller 110 may operate the near infrared ray sensor pixels SAPX and SBPX and the red sensor pixels SAPX and SBPX provided in the row provided near the touch position and provided in the second display region 191a2. Besides this, the controller 110 may combine the example embodiments and may operate the sensor pixels SAPX and SBPX according to the position of the sensor pixels SAPX and SBPX.

In operation S109, the controller 110 measures the heartbeat and/or the saturation of peripheral oxygen (SpO2) of the user by using the change of the amount of light received by the near infrared ray sensor pixels SAPX and SBPX and the red sensor pixels SAPX and SBPX.

In operation S211, the controller 110 compares the heartbeat information measured by a plurality of regions in the edge display regions 190b and 190c, and compares the saturation of peripheral oxygen (SpO2) information measured in a plurality of regions in the edge display regions 190*b* and 190*c*.

In operation S213, when the heartbeat information and the saturation of peripheral oxygen (SpO2) information measured by a plurality of regions are similar to each other (e.g., within 5% of the deviation), the controller 110 outputs the measured heartbeat and saturation of peripheral oxygen (SpO2) information to the edge touch screen 190 or the speaker 163, and stores the same in the storage unit 175. In this instance, like a mean value of a plurality of heartbeat information and a middle value of a plurality of heartbeat information, one selected from among a plurality of heartbeat information is output and stored. In a like manner, like a mean value of a plurality of saturation of peripheral oxygen (SpO2) information and a middle value of a plurality of saturation of peripheral oxygen (SpO2) information, one selected from among a plurality of saturation of peripheral oxygen (SpO2) information is output and stored.

The controller 110 may display heartbeat and saturation of peripheral oxygen (SpO2) information to the edge touch screen 190, or may output the heartbeat and saturation of peripheral oxygen (SpO2) information as a voice through the speaker 163.

Further, the controller 110 may store the heartbeat and saturation of peripheral oxygen (SpO2) information in the storage unit 175, and the user may check his health state in a later time.

In addition, the controller 110 may report the heartbeat and saturation of peripheral oxygen (SpO2) information to an external storage unit or a server through the mobile communicator 120 and the sub-communicator 130.

When a plurality of heartbeat information and saturation of peripheral oxygen (SpO2) information measured by a plurality of regions are different from each other, in operation S215, the controller 110 notifies the user of a restarting of measurement of the heartbeat and the saturation of peripheral oxygen (SpO2) through the output unit 160 such as the edge touch screen 190, the speaker 163, and the vibration motor 164.

According to at least one of example embodiments, the biometrics of the user may be conveniently measured and it may be measured without an additional module, so the inner space of the electronic device 100 may be efficiently used. Hence, the electronic device 100 may become slim or down-sized, and the effect of providing a new user experience to the user is generated.

While example embodiments have been described in connection with some example embodiments, it is to be understood that the example embodiments are not limited to the disclosed example embodiments, but, on the contrary, is intended to cover various modifications and equivalent arrangements included within the spirit and scope of the appended claims.

What is claimed is:

1. An electronic device comprising:
an edge touch screen including a main display region and an edge display region extending from the main display region, each of the main display region and the edge display region including one or more of red pixels, near infrared ray pixels, and sensor pixels for detecting light with different wavelengths, the edge display region including a left edge display region and a right edge display region extending from respective sides of the main display region; and
a controller configured to,
drive the edge touch screen to measure biometrics in the left edge display region and the right edge display region in response to maintaining a multi-touch input in both the left edge display region and the right edge display region for a set time by instructing at least one selected red pixel of the red pixels and at least one selected near infrared ray pixel of the near infrared ray pixels corresponding to a position of the multi-touch input to emit light, and
measure the biometrics in the left edge display region and the right edge display region based on light amounts of light of different wavelengths received from at least one selected sensor pixel of the sensor pixels corresponding to the position of the multi-touch input.

2. The electronic device of claim 1, wherein the edge touch screen includes:
a display panel including the red pixels and the near infrared ray pixels;
a touch panel on the display panel, the touch panel including at least one touch sensor;
a sensor panel including the sensor pixels; and
a light blocking member configured to block part of the display panel from being visible to an outside of the electronic device.

3. The electronic device of claim 2, wherein the at least one selected near infrared ray pixel is in a region of the edge touch screen corresponding to the light blocking member.

4. The electronic device of claim 2, wherein the at least one selected near infrared ray pixel is in the edge display region.

5. The electronic device of claim 2, wherein the at least one selected near infrared ray pixel is in a portion of the main display region adjacent to the edge display region.

6. The electronic device of claim 2, wherein the sensor pixels are in a region of the edge touch screen corresponding to the light blocking member.

7. The electronic device of claim 2, wherein the sensor pixels are in the edge display region.

8. The electronic device of claim 2, wherein at least one of the sensor pixels extends to both the edge display region and a portion of the main display region adjacent to the edge display region.

9. The electronic device of claim 2, wherein the sensor pixels include:
a first sensor pixel configured to detect light of a near infrared ray wavelength, and
a second sensor pixel configured to detect light of a red wavelength, wherein
a size of the first sensor pixel is different from a size of the second sensor pixel.

10. The electronic device of claim 2, wherein
the red pixels and the near infrared ray pixels include organic light emitting diodes (OLEDs), and
the sensor pixels includes organic photodiodes.

11. The electronic device of claim 2, wherein the display panel and the sensor panel are provided on a same layer.

12. The electronic device of claim 1, wherein the controller is configured to drive the edge touch screen to re-measure the biometrics in response to the biometrics measured from the left edge display region and the right edge display region being different from each other.

13. A method for controlling an electronic device, the electronic device including an edge touch screen and a controller, the edge touch screen including a main display region, an edge display region extending from the main display region, each of the main display region and the edge display region including one or more of red pixels, near infrared ray pixels, and sensor pixels for detecting light with different wavelengths, the edge display region including a left edge display region and a right edge display region extending from respective sides of the main display region, the method comprising:

determining whether a multi-touch input respectively on the left edge display region and the right edge display region is maintained for a set time;

instructing one or more selected red pixels of the red pixels and one or more selected near infrared ray pixels of the near infrared ray pixels corresponding to a position of the multi-touch input to emit light in response to determining that the multi-touch input is maintained for the set time;

operating one or more selected sensor pixels of the sensor pixels corresponding to the position of the multi-touch input in the left edge display region and the right edge display region, respectively to receive information from the selected sensor pixels, the information indicating an amount of light of the different wavelengths; and measuring biometrics based on the information.

14. The method of claim 13, wherein the edge touch screen includes:

a display panel including the red pixels and the near infrared ray pixels;

a touch panel on the display panel, the touch panel including at least one touch sensor;

a sensor panel including the sensor pixels; and a light blocking member configured to block part of the display panel from being visible to an outside of the electronic device.

15. The method of claim 14, wherein the one or more selected infrared ray pixels is in at least one of a region corresponding to the light blocking member, the edge display region, and a portion of the main display region adjacent to the edge display region, and the sensor pixels are in at least one of the region corresponding to the light blocking member, the edge display region, and the portion of the main display region adjacent to the edge display region.

16. The method of claim 15, wherein at least one of the sensor pixels extends to both the edge display region and the portion of the main display region adjacent to the edge display region.

17. The method of claim 13, wherein the sensor pixels include:

a first sensor pixel configured to detect light of a near infrared ray wavelength; and a second sensor pixel configured to detect light of a red wavelength, wherein a size of the first sensor pixel is different from a size of the second sensor pixel.

18. The method of claim 13, wherein the red pixels and the near infrared ray pixels include organic light emitting diodes (OLEDs), and the sensor pixels include organic photodiodes.

\* \* \* \* \*